United States Patent [19]

Bestwick et al.

[11] Patent Number: 5,750,864
[45] Date of Patent: May 12, 1998

[54] REGULATED EXPRESSION OF HETEROLOGOUS GENES IN PLANTS

[75] Inventors: Richard Keith Bestwick, Portland; Adolph J. Ferro, Lake Oswego, both of Oreg.

[73] Assignee: Epitope, Inc., Beaverton, Oreg.

[21] Appl. No.: 261,677

[22] Filed: Jun. 17, 1994

[51] Int. Cl.$^6$ .............................. A01H 5/08; A01G 7/00; C12N 15/82; C12N 15/55
[52] U.S. Cl. .............. 800/205; 435/69.1; 435/172.3; 435/195; 536/24.1; 536/23.6; 47/58; 800/DIG. 19; 800/DIG. 37; 800/DIG. 43; 800/DIG. 64; 800/DIG. 65
[58] Field of Search .................... 800/205, DIG. 19, 800/37, 43, 64, 65; 435/69.1, 172.3, 195, 240.4, 320.1; 536/24.1, 23.6; 47/58

[56] References Cited

U.S. PATENT DOCUMENTS 5,416,250 5/1995 Ferro et al. .................... 800/205

FOREIGN PATENT DOCUMENTS

US90/07175 12/1990 WIPO .
WO 92/12249 7/1992 WIPO .
A 94 24294 10/1994 WIPO .

OTHER PUBLICATIONS

Lincoln, J.E., et al., "Regulation of Gene Expression by Ethylene During Lycopersicon esculentum (Tomato) Fruit Development," Proc. Natl. Acad. Sci. USA 84:2793–2797 (1987).
Lincoln, J.E., and Fischer, R.L., "Regulation of Gene Expression by Ethylene in Wild-Type and vin Tomato (Lycopersicon esculentum) Fruit," Plant Physiol. 88:370–374 (1988).
Lincoln, J.E., and Fischer, R.L., "Diverse Mechanisms for the Regulation of Ethylene-Inducible Gene Expression," Mol. Gen. Genet. 212:71–75 (1988).
Bestwick, R.K., et al., "Decreased Ethylene Synthesis and Altered Fruit Ripening in Transgenic Tomatoes Expressing S–Adenosylmethionine Hydrolase," HortScience 29:474, abstract No. 306 (1994).
Bestwick, R.K., et al., Reduced Ethylene Synthesis and Suspended Fruit Ripening in Transgenic Tomatoes Expressing S–Adenosylmethionine Hydrolase, J. Cell. Biochem. Suppl. 0(16 part a):98 abstract No. X1–208 (1994).
Deikman, J., et al., Organization of Ripening and Ethylene Regulatory Regions in a Fruit-Specific Promoter from Tomato (Lycopersicon esculentum) Plant Physiol. 100:2013–2017 (1992).
Langhoff, D., et al., "Effect of S–Adenosylmethionine Hydrolase Expression on Ethylene Biosynthesis in Transgenic Tomatoes," J. Chem. Biochem. Suppl. 0 (16 part F), abstract No. Y307, (1992).
Mathews, H., et al., "Genetic Transformation of Red Raspberry with a Gene to Control Ethylene Biosynthesis," HortScience 29:445, abstract No. 180 (1994).
Montgomery, J., et al., "Identification of an Ethylene–Responsive Region in the Promoter of a Fruit-Ripening Gene," Proc. Natl. Acad. Sci. USA 90:5939–5943 (1993).
Lewin (1987) Science 237:70.
Benfey et al (1990) Science 250:959–966.
Smith et al (1988) Nature 334:724–726.
Hughes et al (1987) Nucl. Acids Res 75(2):717–729.
Klee et al (1991) The Plant Cell 3:1187–1193.
Sturm et al (1990) The Plant Cell 2:1107–1119.
Cordes et al (1989) The Plant Cell 1:1025–1034.

Primary Examiner—Elizabeth McElwain
Attorney, Agent, or Firm—Susan T. Evans; Gary R. Fabian; Peter J. Dehlinger

[57] ABSTRACT

The use of AdoMetase to reduce ethylene biosynthesis in plants is facilitated by the exploitation of the tissue and stage specific properties of the E4 promoter from tomato.

The E4 promoter, isolated from tomato or other plants by methods described herein, provides a useful regulatable promoter for the expression of a variety of heterologous genes, including the AdoMetase gene.

10 Claims, 20 Drawing Sheets

```
   1 gaattctcaa  tgagcccaa ttcaatctcc aatttcaacc cgttttaaaa cttttattta
  61 agatatgttt  tatattgaa agtatgaatt attatctatt taacatcttt taggatttat
 121 ctatccattt  gctacttttt taacaaaaaa ttcttgagtg aaaattcaaa ttgtgattat
 181 aaaagttaaa  tatcaatatg ttaaattatt aagattaatc gggtcaaatt ggcgggtcaa
 241 ggcccaattc  tttttagcc catttaagct caaagtaaac ttgggtgggt caagacccaa
 301 ctcgatttct  gttcaaccca ttttaatatt tctattttca acctaacccg ctcatttgat
 361 acccctacaa  atatcatatt tgtgtgtgaa atatttttg ggctggagag agaggccccg
 421 aggggagtgg  aggggtgggg tggggagaga gagcgagaaa gagtggagag agaaatttga
 481 tatgaaatcc  tacatatatt acagattgta atgttctaaa ctataacgat tgtcataaa
 541 cacatatcat  ggatttgtct ttttgtgtaa ttttcccaat tgtaaatagg acttcgttat
 601 ttgaaacttg  aaagtgaagt cacatagatt aagtacaaac attaattaaa gaccgtggtg
 661 gaatgataaa  tatttattta tctttaatta gttattttt tgggagctct ttattccaat
 721 gtgagacttt  tgcgacatat attcaaattt aatcgaatca caatatgtat tagattgata
 781 aaaaaataat  tttttacaa tgttagttga gactcataac ttactgccta ttggtaatct
 841 atgactccta  attccttaat tatttaaata tatcatcttg atcgttaaca aagtaatttc
 901 gaaagaccac  gagtaagaag acaaacgaga ataccaaaaa attcaaaaat ttaatgtgat
 961 ttggtcaatc  gatctacgtc cataaaggag atgagtaatc tactataaat atgagagtac
1021 aaaatacaga  gagaaacaac ctcaactaat tcactcggaa tacatgagaa gttcacacaa
1081 gtgataacgt  atcaaacttg tgacccacac ttttccctct aaccaaagct cttaaaacta
1141 tattgtgaat  gctgattaag ttaaacgaaa cagtcctaaa tcttttccgt cctatgagaa
1201 acaagattaa  tcaattcaca atttttttaa aaagaaaaac ctgtaagaaa tttaggcaaa
1261 caaaacctaa  cacaagtttg ttttgtttt tactaccaac aagaaattca aatggcaaat
1321 gtataacgca  tcttagctaa ttatatgacc agattcagat taatatacat cttcacccat
1381 gcaatccatt  tctatataaa gaaacataca cgaacttgat attattagag attgagcaat
1441 ggagggtaac  aacagcagta gcaagtcaac caccaatcca gcattggatc cggatctgga
1501 cagcccggat  cagccgggtc tggagtttgc ccaatttgct gccggctgct tttggggagt
1561 cgaattggct  ttccagaggg ttggaggagt agtgaagacg gaggttgggt actctcaggg
1621 gaatgtccat  gacccgaact acaagcttat ttgctccgga acaaccgaac atgccgaggc
1681 cattcggatc  cagtttgacc cgaatgtctg cccgtattcc aatctccttt ctctatttg
1741 gagtcgccat  gacccgacca ctctaaatcg ccaggtatca aattcctttg tgtttcatt
1801 ttatgtgatt  aatattaaaa attttttata taatgtcat gatgatggtt gttgctaggg
1861 taatgatgtg  ggaaagcaat accgctcagg aatatattac tataatgatg ctcaggctca
1921 actggcaagg  gagtcgttag aagctaagca gaaggaattt atggataaga aaattgtcac
1981 tgaaattctt  cctgctaaga gatttatag agctgaagag tatcaccagc aatatctaga
2041 gaagggtggg  ggcagaggtt gtaagcagtc ggctgcaaag ggctgcaatg acccaataag
2101 gtgctacggt  tgacagcaga tctttgaatg tcatagcaac tacaaaagaa cttgttagac
2161 atttgctgtc  ttgcttcttt aaatttgaat aaacatgaca atgattctta taactacttg
2221 ctctcttgga  tggaataact agttgtcgta agtattctc ctcttgctaa ttattatctc
2281 tctttatatg  gtacctgcaa tttgttgctt tagttacaga ataatggacg tcaattctat
2341 atcttaattt  gttttaagtc ttaaatgagg tggtttgtgt ttgaaagcaa tatcaagcat
2401 agtaatacca  atgatttagt agatgaactt aatcaaatca aattccaaaa tgcagtctac
2461 aaattgacaa  catgaagtta agtgtatctt atgtaaattg acatctttcc tagtagatgc
2521 ctaatacttt  tgtaaagact aaaataagca cagatgaggc ttgtgcattt aacttagagt
2581 tcatccttag  gtgtggctgc aggagaccct gtagggttgc ttgaagtctt gatggggtag
2641 gagggttgca  ttgctatacc acacaacccc tcttcagcgt caaccttgcg ctgcattcta
2701 atgtatcctt  tttctcccca ttcagctccc catgagttct tcacaatcca gtatttggtt
2761 ccatcgacgg  ttgtgccata ccccacaata gccaca
```

Fig. 13

>Hind3

```
           10         20         30         40         50         60         70
            *          *          *          *          *          *          *
AAGCTTAAAG TAAACTTGGG TGGGTCAAGA CCCAACTCGA TTTCTGTTCA ACCCATTTTA ATATTTCTAT
_____>
       b          b        TOMATO E4 PROMOTER        b          b           >

80         90        100        110        120        130        140
            *          *          *          *          *          *          *
TTTCAACCTA ACCCGCTCAT TTGATACCCC TACAAATATC ATATTTGTGT GTGAAATATT TTTTGGGCTG
       b          b        TOMATO E4 PROMOTER        b          b           >

150        160        170        180        190        200        210
            *          *          *          *          *          *          *
GAGAGAGAGG CCCCGAGGGG AGTGGAGGGG TGGGGTGGGG AGAGAGAGCG AGAAAGAGTG GAGAGAGAAA
       b          b        TOMATO E4 PROMOTER        b          b           >

220        230        240        250        260        270        280
            *          *          *          *          *          *          *
TTTGATATGA AATCCTACAT ATATTACAGA TTGTAATGTT CTAAACTATA ACGATTTGTC ATAAACACAT
       b          b        TOMATO E4 PROMOTER        b          b           >

290        300        310        320        330        340        350
            *          *          *          *          *          *          *
ATCATGGATT TGTCTTTTTG TGTAATTTTC CCAATTGTAA ATAGGACTTC GTTATTTGAA ACTTGAAAGT
       b          b        TOMATO E4 PROMOTER        b          b           >

360        370        380        390        400        410        420
            *          *          *          *          *          *          *
GAAGTCACAT AGATTAAGTA CAAACATTAA TTAAAGACCG TGGTGGAATG ATAAATATTT ATTTATCTTT
       b          b        TOMATO E4 PROMOTER        b          b           >

430        440        450        460        470        480        490
            *          *          *          *          *          *          *
AATTAGTTAT TTTTTTGGGA GCTCTTTATT CCAATGTGAG ACTTTTGCGA CATATATTCA AATTTAATCG
       b          b        TOMATO E4 PROMOTER        b          b           >

500        510        520        530        540        550        560
            *          *          *          *          *          *          *
AATCACAATA TGTATTAGAT TGATAAAAAA ATAATTTTTT TACAATGTTA GTTGAGACTC ATAACTTACT
       b          b        TOMATO E4 PROMOTER        b          b           >

570        580        590        600        610        620        630
            *          *          *          *          *          *          *
GCCTATTGGT AATCTATGAC TCCTAATTCC TTAATTATTT AAATATATCA TCTTGATCGT TAACAAAGTA
       b          b        TOMATO E4 PROMOTER        b          b           >

640        650        660        670        680        690        700
            *          *          *          *          *          *          *
ATTTCGAAAG ACCACGAGTA AGAAGACAAA CGAGAATACC AAAAAATTCA AAAATTTAAT GTGATTTGGT
       b          b        TOMATO E4 PROMOTER        b          b           >
```

Fig. 14A

```
            710         720         730         740         750         760         770
             *     *     *     *     *     *     *     *     *     *     *     *     *     *
CAATCGATCT ACGTCCATAA AGGAGATGAG TAATCTACTA TAAATATGAG AGTACAAAAT ACAGAGAGAA
_____b_____b_____TOMATO E4 PROMOTER_____b_____b_____>

780         790         800         810         820         830         840
             *     *     *     *     *     *     *     *     *     *     *     *     *     *
ACAACCTCAA CTAATTCACT CGGAATACAT GAGAAGTTCA CACAAGTGAT AACGTATCAA ACTTGTGACC
_____b_____b_____TOMATO E4 PROMOTER_____b_____b_____>

850         860         870         880         890         900         910
             *     *     *     *     *     *     *     *     *     *     *     *     *     *
CACACTTTTC CCTCTAACCA AAGCTCTTAA AACTATATTG TGAATGCTGA TTAAGTTAAA CGAAACAGTC
_____b_____b_____TOMATO E4 PROMOTER_____b_____b_____>

920         930         940         950         960         970         980
             *     *     *     *     *     *     *     *     *     *     *     *     *     *
CTAAATCTTT TCCGTCCTAT GAGAAACAAG ATTAATCAAT TCACAATTTT TTTAAAAAGA AAAACCTGTA
_____b_____b_____TOMATO E4 PROMOTER_____b_____b_____>

990        1000        1010        1020        1030        1040        1050
             *     *     *     *     *     *     *     *     *     *     *     *     *     *
AGAAATTTAG GCAAACAAAA CCTAACACAA GTTTGTTTTT GTTTTTACTA CCAACAAGAA ATTCAAATGG
_____b_____b_____TOMATO E4 PROMOTER_____b_____b_____>

1060        1070        1080        1090        1100        1110        1120
             *     *     *     *     *     *     *     *     *     *     *     *     *     *
CAAATGTATA ACGCATCTTA GCTAATTATA TGACCAGATT CAGATTAATA TACATCTTCA CCCATGCAAT
_____b_____b_____TOMATO E4 PROMOTER_____b_____b_____>

>NcoI
                                                                   |
           1130        1140        1150        1160        1170    |    1180
             *     *     *     *     *     *     *     *     *     *  |  *     *     *
CCATTTCTAT ATAAAGAAAC ATACACGAAC TTGATATTAT TAGAGATTGA GCC ATG GTT TTC ACT
                                                            Met Val Phe Thr>
                                                            ___e_SAMK__e___>
_____b_____TOMATO E4 PROMOTER_____b_____b_>
                                                     ___KOZAK LINKER___>

>XmnI
             |
           1190        1200 |      1210        1220        1230        1240
             *     *     *  |  *     *     *     *     *     *     *     *     *     *
AAA GAG CCT GCG AAC GTC TTC TAT GTA CTG GTT TCC GCT TTC CGT TCT AAC CTC TGC
Lys Glu Pro Ala Asn Val Phe Tyr Val Leu Val Ser Ala Phe Arg Ser Asn Leu Cys>
___e___e___e___e___e___e___e___e___SAMase__e___e___e___e___e___e___e___e___>
_KOZAK LINKER_____>
```

Fig 14B

```
                 1250        1260        1270        1280        1290
       *      *     *      *     *      *     *      *     *      *
GAT GAG GTG AAT ATG AGC AGA CAC CGC CAC ATG GTA AGC ACT TTA CGT GCC GCA CCG
Asp Glu Val Asn Met Ser Arg His Arg His Met Val Ser Thr Leu Arg Ala Ala Pro>
___e___e___e___e___e___e___e___e___SAMase__e___e___e___e___e___e___e___e___>

1300        1310        1320        1330        1340        1350
   *      *     *      *     *      *     *      *     *      *     *     *
GGT CTT TAT GGC TCC GTT GAG TCA ACC GAT TTG ACC GGG TGC TAT CGT GAG GCA ATC
Gly Leu Tyr Gly Ser Val Glu Ser Thr Asp Leu Thr Gly Cys Tyr Arg Glu Ala Ile>
___e___e___e___e___e___e___e___e___SAMase__e___e___e___e___e___e___e___e___>

1360        1370        1380        1390        1400        1410
      *      *     *      *     *      *     *      *     *      *     *
TCA AGC GCA CCA ACT GAG GAA AAA ACT GTT CGT GTA CGC TAC AAG GAC AAA GCG CAG
Ser Ser Ala Pro Thr Glu Glu Lys Thr Val Arg Val Arg Tyr Lys Asp Lys Ala Gln>
___e___e___e___e___e___e___e___e___SAMase__e___e___e___e___e___e___e___e___>

1420        1430        1440        1450        1460        1470
         *      *     *      *     *      *     *      *     *      *     *
CCA CTC AAT GTT GCA CGC CTA GCT TCT AAT GAG TGG GAG CAA GAT TGC GTA CTG GTA
Pro Leu Asn Val Ala Arg Leu Ala Ser Asn Glu Trp Glu Gln Asp Cys Val Leu Val>
___e___e___e___e___e___e___e___e___SAMase__e___e___e___e___e___e___e___e___>

1480        1490        1500        1510        1520
              *      *     *      *     *      *     *      *     *      *     *
TAC AAA TCA CAG ACT CAC ACG GCT GGT CTG GTG TAC GCT AAA GGT ATC GAC GGG TAT
Tyr Lys Ser Gln Thr His Thr Ala Gly Leu Val Tyr Ala Lys Gly Ile Asp Gly Tyr>
___e___e___e___e___e___e___e___e___SAMase__e___e___e___e___e___e___e___e___>

1530        1540        1550        1560        1570        1580
   *      *     *      *     *      *     *      *     *      *     *
AAG GCT GAA CGT CTG CCG GGT AGT TTC CAA GAG GTT CCT AAA GGC GCA CCG CTG CAA
Lys Ala Glu Arg Leu Pro Gly Ser Phe Gln Glu Val Pro Lys Gly Ala Pro Leu Gln>
___e___e___e___e___e___e___e___e___SAMase__e___e___e___e___e___e___e___e___>

>Stop Codon
                                                       |
  1590        1600        1610        1620        1630|       1640
   *      *     *      *     *      *     *      *     *      *|    *      *
GGC TGC TTC ACT ATT GAT GAG TTC GGT CGC CGC TGG CAA GTA CAA TAA CGTGTTAA
Gly Cys Phe Thr Ile Asp Glu Phe Gly Arg Arg Trp Gln Val Gln ***
___e___e___e___e___e___e___SAMase__e___e___e___e___e___e___e___>

>Kpn I
                          |
     1650        1660     1670   1678
      *      *     *      *     *      *     *
ACTCAAGGTC ATGCACGATG CGTGGCGGAT CGGGTACC
```

Fig 14C

```
Sequence Range: 1402 to 2035 of Tomato E4 from Fischer
                 1410       1420       1430       1440       1450
                  *    *     *    *     *    *     *    *     *    *     *
TomE4 -Fis  AAACATACA CGAACTTGAT ATTATTAGAG ATTGAGCA ATG GAG GGT AAC AAC
AGC                                                   Met Glu Gly Asn Asn
Ser>
                                                      ___a__E4 EXON
1____a___>

1460       1470       1480       1490       1500
                  *    *     *    *     *    *     *    *     *    *
TomE4 -Fis  AGT AGC AAG TCA ACC ACC AAT CCA GCA TTG GAT CCG GAT CTG GAC AGC
            Ser Ser Lys Ser Thr Thr Asn Pro Ala Leu Asp Pro Asp Leu Asp
Ser>
            ___a___a___a___a___a___a__E4 EXON
1____a___a___a___a___a___a___>

1510       1520       1530       1540       1550
                  *    *     *    *     *    *     *    *     *    *
TomE4 -Fis  CCG GAT CAG CCG GGT CTG GAG TTT GCC CAA TTT GCT GCC GGC TGC TTT
            Pro Asp Gln Pro Gly Leu Glu Phe Ala Gln Phe Ala Ala Gly Cys
Phe>
            ___a___a___a___a___a___a__E4 EXON
1____a___a___a___a___a___a___>

1560       1570       1580       1590       1600
                  *    *     *    *     *    *     *    *     *    *
TomE4 -Fis  TGG GGA GTC GAA TTG GCT TTC CAG AGG GTT GGA GGA GTA GTG AAG ACG
            Trp Gly Val Glu Leu Ala Phe Gln Arg Val Gly Gly Val Val Lys
Thr>
            ___a___a___a___a___a___a__E4 EXON
1____a___a___a___a___a___a___>
                        |          |     40    |    50    |    60    |
 Rasp. E4               |          |           |          |          |
                   _____GAG CTC AGG TTT CAG cGa GTg Gcc GGt GTg GTc AAG
ACc>
                   |    ^^_ _^_ ___ ^^_ ^^^ _^_ ^^_ ^__ ^^_ ^^_ ^^_ ^^^ ^^_
TomE4 -Fis         |    GAA TTG GCT TTC CAG AGG GTT GGA GGA GTA GTG AAG ACG 1610       1620       1630       1640
                  *    *     *    *     *    *     *    *     *
TomE4 -Fis  GAG GTT GGG TAC TCT CAG GGG AAT GTC CAT GAC CCG AAC TAC AAG CTT
            Glu Val Gly Tyr Ser Gln Gly Asn Val His Asp Pro Asn Tyr Lys
Leu>
            ___a___a___a___a___a___a__E4 EXON
1____a___a___a___a___a___a___>
                  |          |           |          |          |
 Rasp. E4         70         |    80     |    90    |   100    |   110
            GAG GTT GGG TAC TCc CAG GGc cAc GTC CAc GAt CCG AAt TAC AAa
CTg>
            ^^^ ^^^ ^^^ ^^^ ^^_ ^^^ ^^_ _^_ ^^^ ^^_ ^^_ ^^^ ^^_ ^^^ ^^_
TomE4 -Fis  GAG GTT GGG TAC TCT CAG GGG AAT GTC CAT GAC CCG AAC TAC AAG CTT
```

Fig. 15A

```
             1650        1660         1670         1680         1690
              *        *    *       *    *       *    *       *    *       *
TomE4 -Fis   ATT TGC TCC GGA ACA ACC GAA CAT GCC GAG GCC ATT CGG ATC CAG TTT
             Ile Cys Ser Gly Thr Thr Glu His Ala Glu Ala Ile Arg Ile Gln
Phe>
               ___a___a___a___a___a___a__E4 EXON
1____a___a___a___a___a___a___>
                  |          |           |          |           |
  Rasp. E4        |    120   |     130   |    140   |     150   |
             gTc TGC TCC GGA ACt ACC aAc CAT tCg GAG GtC gTT CGG gTC CAG
TTc>
             _^_ ^^^ ^^^ ^^^ ^^_ ^^^ _^_ ^^^ _^_ ^^^ ^_^ _^^ ^^^ _^^ ^^^ ^^_
TomE4 -Fis   ATT TGC TCC GGA ACA ACC GAA CAT GCC GAG GCC ATT CGG ATC CAG TTT 1700         1710         1720         1730         1740
              *        *    *       *    *       *    *       *    *
TomE4 -Fis   GAC CCG AAT GTC TGC CCG TAT TCC AAT CTC CTT TCT CTA TTT TGG AGT
             Asp Pro Asn Val Cys Pro Tyr Ser Asn Leu Leu Ser Leu Phe Trp
Ser>
               ___a___a___a___a___a___a__E4 EXON
1____a___a___a___a___a___a___>
                |           |          |           |           |
Rasp. E4   160  |     170   |    180   |     190   |     200   |
             GAC CCG cAa GTC TaC CCa TAc TCg gAc CTg CTT TCc gTc TTT TGG
tcT>
             ^^^ ^^^ _^_ ^^^ ^_^ ^^_ ^^_ ^^_ _^_ ^^_ ^^^ ^^_ _^_ ^^^ ^^^ __^
TomE4 -Fis   GAC CCG AAT GTC TGC CCG TAT TCC AAT CTC CTT TCT CTA TTT TGG AGT 1750         1760         1770         1780         1790
              *        *    *       *    *       *    *       *    *       *
TomE4 -Fis   CGC CAT GAC CCG ACC ACT CTA AAT CGC CAG GTATCA AATTCCTTTG
             Arg His Asp Pro Thr Thr Leu Asn Arg Gln>
               ___a___a___a__E4 EXON 1____a___a___a___>
                                                              _____INTRON_____>
                                                            |
Rasp. E4   210  |      220  |      230  |      240  |
             CGt CAT GAt CCa ACg ACT gTc AAT CGC CAG GTATgg ggaTtg>         |
             ^^_ ^^^ ^^_ ^^_ ^^_ ^^^ _^_ ^^^ ^^^ ^^^ ^^^^__ ___^__         |
TomE4 -Fis   CGC CAT GAC CCG ACC ACT CTA AAT CGC CAG GTATCA AATTCC          |
```

Fig. 15B ns by extracting the nutrients from it. CA storage can also lead to undesirable side effects: injury can result from high $CO_2$ levels, low $O_2$ levels, or low temperature.-->

REGULATED EXPRESSION OF HETEROLOGOUS GENES IN PLANTS

FIELD OF THE INVENTION

The present invention relates to the regulated expression of heterologous genes in plants using the E4 promoter.

REFERENCES

Adams, D. O., and Yang, S. F., *Plant Physiology* 70:117–123 (1977).

An, G., et al., *Plant Mol. Biol. Man.* A3:1–19 (abstract) (1988).

An, G., et al., *EMBO J.* 4:277–284 (1985).

Becker, D., et al., *Plant Mol. Biol.* 20:1195–1197 (1992).

Bellini, C., et al., *Bio/Technol* 7(5):503–508 (1989).

Comai, L. and Coning, A. J., U.S. Pat. No. 5,187,267, issued 16 Feb. 1993.

Cordes, S., et al., *The Plant Cell* 1:1025–1034 (1989).

Dayhoff, M. O., in *Atlas of Protein Sequence and Structure* (1972) Vol. 5, National Biomedical Research Foundation, pp. 101–110, and Supplement 2 to this volume, pp. 1–10.

Fillatti, J. J., et al., *Biotechnology* 5:726–730 (1987).

Fritsch, et al., in *MOLECULAR CLONING: A LABORATORY MANUAL*, Cold Spring Harbor Lab, Cold Spring Harbor, N.Y. (1989).

Gallie, D. R., *Ann. Rev. Plant Physiol. and Plant Mol. Biol.* 44:77–105 (1993).

Giovannoni, J. J., et al., *Plant Cell* 1:53–63 (1989).

Goding, J. W., *J. Immun. Methods* 39:285–308 (1980).

Hamilton, A. J., et al., *Nature* 346:284–287 (1990).

Hood, E., et al., *J. Bact.* 168:1291–1301 (1986).

Horsten, K. H., et al., *J. Gen. Virol.* 43:57–73 (1979).

Houck, C. M. and Pear, J. R., U.S. Pat. No. 4,943,674, issued 24 Jul. 1990.

Hughes, J. A., et al., *J. Bact.* 169:3625–3632 (1987a).

Hughes, J. A., et al., *Nuc. Acid. Res.* 15:717–729 (1987b).

Imaseki, H., "The biochemistry of ethylene biosynthesis" in *THE PLANT HORMONE ETHYLENE (Matoo, A. K., and Suttle, J. C., Eds.), CRC Press*, pp. 1–20 (1991).

Joshi, C. P., *Nuc. Acid Res.* 16:6643–6653 (1987).

Kende, H., *Plant Physiol.* 91:1–4 (1989).

Kende, H., *Ann. Rev. Plant Physiol. and Plant Mol. Biol.* 44:282–307 (1993).

Klee, H. J., et al., *Plant Cell* 3:1187–1193 (1991).

Klein, T. M., et al., *PNAS (USA)* 85(22):8502–8505 (1988).

Kozak, M., *Mol. Cell Biol.* 9:5073–5080 (1989).

Kushad, M. M., et al., *Plant Physiol.* 73:257–251 (1983).

Lincoln, J. E., et al., *Proc. Natl. Acad. Sci. USA* 84:2793–2797 (1987).

Lincoln, J. E., and Fischer, R. L., *Plant Physiol.* 88:370–374 (1988).

Lutcke, H. A., et al., *EBMO J.* 6:43–48 (1987).

Mertens, H., et al., *J. Gen. Virol.* 62:331–341 (1982).

Miki, B. L. A., et al., *Plant DNA Infectious Agents* (Hohn, T., et al., eds.) Springer-Verlag, Wien, Austria, pp.249–265 (1987).

Mullis, K. B., U.S. Pat. No. 4,683,202, issued 28 Jul. 1987.

Mullis, K. B., et al., U.S. Pat. No. 4,683,195, issued 28 Jul. 1987.

Nagel, R., et al., *FEMS Microbiol. Lett.* 67:325–327 (1990).

Oeller, P. W., et al., *Science* 254:437–139 (1991).

Sambrook, J., et al., In *Molecular Cloning: A Laboratory Manual*, Cold Spring Harbor Laboratory Press, Vol. 2 (1989).

Studier, F. W., and Movva, N. R., *J. Virol.* 19:136–145 (1993).

Theologis, A., *Cell* 70:181–184 (1992).

Ward, T. M., et al., *ANALYTICAL PROCEDURES FOR THE ASSAY AND IDENTIFICATION OF ETHYLENE* (Hillman, J., Ed.) Cambridge University Press, Cambridge, Mass., pp. 135–151 (1978).

BACKGROUND OF THE INVENTION

Ethylene is a plant hormone which is a powerful regulator of plant metabolism, acting, and interacting with other plant hormones in trace amounts. Ethylene is a gas under normal physiological conditions. Even at low concentrations, ethylene has profound hormonal effects on plants.

The effects of ethylene, whether produced by the plant itself or applied exogenously, are numerous, dramatic, and of considerable commercial importance. Among the diverse physiological effects are the following: leaf abscission; fading in flowers; flower wilting; leaf yellowing; leaf epinasty; and stimulation of ripening in fruits and vegetables. Ethylene promotes senescence in plants, both in selected groups of cells and in whole organs, such as, fruits, leaves, or flowers. Senescence is the natural, genetically controlled degenerative process which usually leads to death in plants.

Normally, ethylene production from plant tissue is low. Large quantities of ethylene, however, are produced during ripening and senescence processes. A large amount of ethylene is also produced following trauma caused by chemicals, temperature extremes, water stress, ultraviolet light, insect damage, disease, or mechanical wounding. Ethylene produced by plants under such trauma conditions is referred to as "wound ethylene" or "stress ethylene". In fruits and vegetables, the stimulation of ethylene production by cuts or bruises may be very large and bear considerably on storage effectiveness. Ethylene-induced leaf browning is a common basis for loss in many plants, including lettuce and tobacco. In some tissues, exposure to only a small amount of ethylene may cause an avalanche of ethylene production in adjacent plants or plant tissues such as fresh produce. This autocatalytic effect can be very pronounced and lead to loss of fruit quality during transportation and storage.

Current technologies that specifically address post-harvest storage life have been in existence for decades and are hampered by such problems as high cost, side effects, and an inability to completely shut off ethylene production. Included in this group are controlled atmosphere (CA) storage, chemical treatment, packaging, and irradiation.

CA facilities slow ethylene biosynthesis through: (i) low temperature, (ii) reducing the oxygen level below 3%, and (iii) elevating the carbon dioxide level in the storage area to the 3%–5% range. Expensive scrubbers are sometimes added which reduce ethylene already respired to the atmosphere. Drawbacks are that CA facilities are expensive to construct, have a high utility cost, and are unable to completely eliminate ethylene production and side effects. Also, CA storage techniques can only control external ethylene and not that which resides inside the plant tissue. CA storage can also lead to undesirable side effects: injury can result from high $CO_2$ levels, low $O_2$ levels, or low temperature.

Another treatment is to limit the ethylene biosynthesis in the plant tissue through chemical treatment. Aminoethoxyinylglycine (AVG), an analog of the antibiotic rhizobitoxine, is one such inhibitor. However, AVG cannot be used as a chemical additive in foods due to its high toxicity. Silver thiosulfate (STS) is also effective in slowing fruit ripening and flower fading, but is also toxic and cannot be used on foods. Further, STS only works with certain flowers and often causes black spotting.

Recently, molecular genetic approaches leading to transgenic plants with impaired biosynthesis of ethylene have been reported. Hamilton, et al., identified a cDNA clone for tomato EFE (pTOM13) by inhibiting ethylene synthesis with an antisense gene expressed in transgenic plants. Oeller, et al., showed that expression of antisense RNA to the rate-limiting enzyme in the biosynthetic pathway of ethylene, 1-aminocyclopropane-1-carboxylate synthase, inhibits fruit ripening in tomato plants. Klee, et al., cloned the gene encoding ACC deaminase, from soil bacteria, and introduced it into tomato plants. Reduction in ethylene synthesis in transgenic plants did not cause any apparent vegetative phenotypic abnormalities. However, fruits from these plants exhibited significant delays in ripening, and the mature fruits remained firm for at least 6 weeks longer than the non-transgenic control fruit.

SUMMARY OF THE INVENTION

The present invention includes, in one embodiment, a method for delaying ripening of the fruit of a fruit-bearing plant. The method includes transforming plant progenitor cells, or host cells, with a selectable vector containing a plant E4 gene promoter and a heterologous gene, such as S-adenosylmethionine hydrolase, whose product reduces ethylene biosynthesis in the plant. The transformed cells are grown to produce a transgenic plant bearing fruit. In a related embodiment, the method is used, essentially as above, to delay senescence in flowers and vegetables. The E4 promoter, and/or the transformed plant, may be selected from a variety of plants, including fruit-bearing plants, such as tomato, eggplant, legumes, raspberry, strawberry, melon, avocado, cherry, apricot, citrus fruits, etc.; flowers, such as roses and carnations; and vegetables, such as cauliflower, and lettuce.

In another aspect, the invention includes a method of isolating E4 promoters from plants. The method includes selecting an E4 probe, hybridizing it with genomic DNA from selected plant species, identifying DNA or clones from positively-hybridizing targets, and isolating promoter sequences associated with the positive target molecule. Positively-hybridizing targets can be identified by either primary or secondary detection of reporter moieties attached to the probe. The probe can be obtained by a number of methods, including primer-based DNA amplification or isolation of restriction digest fragments.

In another embodiment, the invention includes a delayed-ripening fruit, containing a heterologous gene, such as the S-adenosylmethionine hydrolase gene, and a promoter, such as the E4 promoter, effective to produce transient expression of the heterologous gene when the fruit is picked. The promoter may be obtained from a variety of plants, such as outlined above, using methods of the present invention.

Also included in the present invention is an E4 promoter molecule and a DNA construct containing the promoter molecule operably linked to a heterologous gene, where expression of the heterologous gene is under the control of the promoter DNA molecule.

These and other objects and features of the invention will be more fully appreciated when the following detailed description of the invention is read in conjunction with the accompanying drawings.

BRIEF DESCRIPTION OF THE FIGURES

FIG. 2B schematically illustrates the effect of the enzyme SAMase (AdoMetase) on ethylene biosynthesis.

FIG. 13 shows the DNA sequence of the tomato E4 gene.

FIG. 14(1)–(3) show the DNA sequence of a HindIII/ KpnI fragment containing the tomato E4 promoter and the SAMase gene, and the translated amino acid sequence of the SAMase gene.

FIG. 15(1) and (2) show a DNA sequence alignment of a region of the tomato E4 gene with a DNA fragment isolated from a raspberry genomic DNA library.

DETAILED DESCRIPTION OF THE INVENTION

I. Definitions

Figure 1:
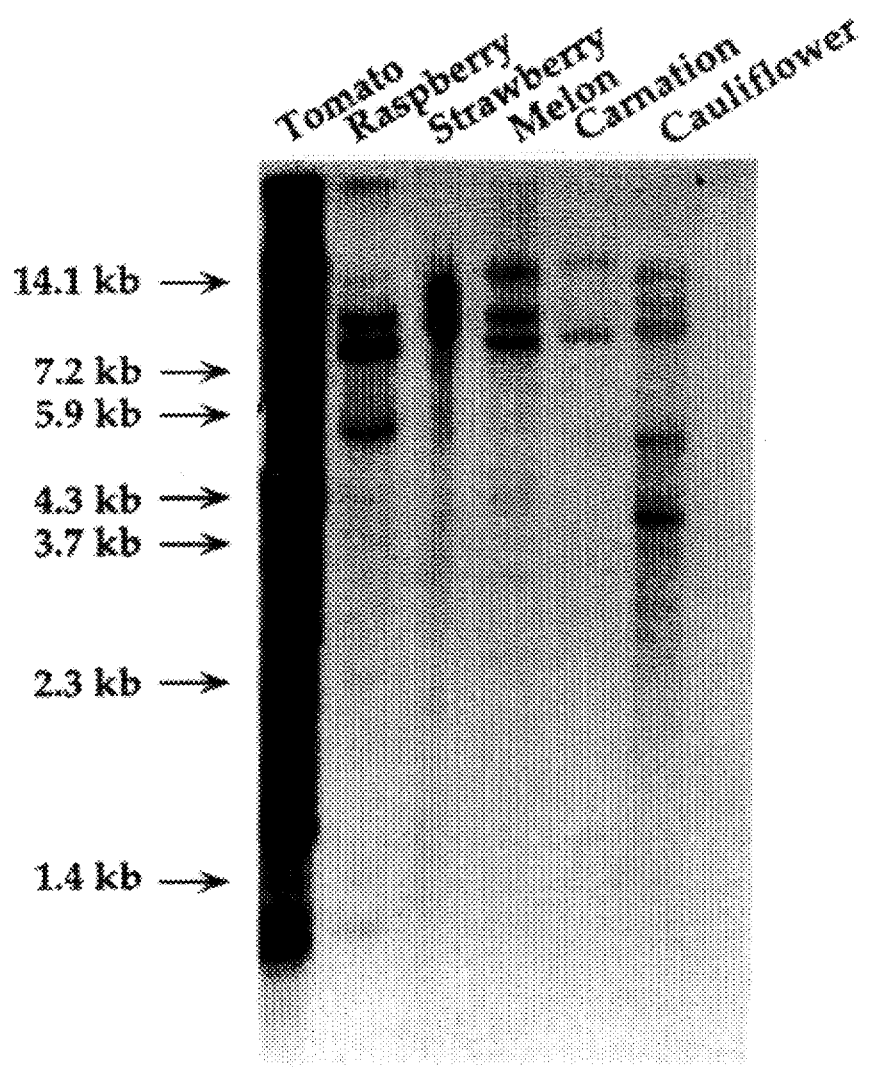
FIG. 1 shows a photograph of an autoradiogram of a Southern blot of tomato, raspberry, strawberry, melon, carnation and cauliflower DNA probed with a fragment containing the coding sequence from the tomato E4 gene.

Heterologous DNA refers to DNA which has been transfected into a host organism. Typically, heterologous DNA refers to DNA that is not originally derived from the transfected or transformed cells' genomic DNA (e.g., CAT and β-galactosidase gene sequences). However, any DNA introduced into an organism by recombinant means is referred to as heterologous DNA (e.g., introduction into a tomato of a vector carrying the tomato E4 promoter).

Two nucleotide sequences are considered to be functionally homologous if they hybridize with one another under moderately stringent conditions, i.e. 0.1% SSC at room temperature. Typically, two homologous nucleotide sequences are greater than or equal to about 60% identical when optimally aligned using the ALIGN program (Dayhoff).

Two amino acid sequences are considered homologous if their amino acids are greater than or equal to about 60% identical when optimally aligned using the ALIGN program mentioned above.

II. E4 Promoters

The present invention provides, in one aspect, nucleic acid constructs suitable for transforming plants with heterologous genes under the control of an E4 promoter (originally isolated from tomato; Cordes, et al.). In one embodiment, the plant is a fruit-bearing plant, and the heterologous gene is a gene effective to reduce ethylene biosynthesis in fruit from the plant. In another embodiment, the plant is a flowering plant, and the heterologous gene is a gene effective to reduce ethylene biosynthesis in flowers of the plant. In still another embodiment, the plant is a vegetable, and the heterologous gene is a gene effective to reduce ethylene biosynthesis in the vegetable.

Experiments performed in support of the present invention demonstrate that an exemplary heterologous gene effective to reduce ethylene biosynthesis in tissues of a plant is the AdoMetase gene, isolated from bacteriophage T3 (Hughes, et al., 1987a). These experiments show that ethylene production in ripe transgenic tomatoes containing the AdoMetase gene under the control of the tomato E4 promoter is significantly lower. In addition, the tomatoes develop color to a light red stage and then cease further color development, and remain firm longer than control tomatoes. Further, the experiments show that an E4 promoter coupled to a heterologous gene can be activated by wounding plant tissue containing the construct, and that the activation of the promoter is typically transient in nature.

A. Tomato E4 Promoter

The tomato E4 promoter is both stage and tissue specific (Cordes, et al.). Typically, E4 mRNA is abundant in ripening fruit and is not detected in leaf, root, stem, or unripe fruit. E4 gene expression can, however, be activated by ethylene, and the ethylene-induced expression can be detected in a variety of plant tissues (Lincoln, et al., Lincoln and Fischer). Further, the rin (ripening inhibited) mutation, that blocks many aspects of ripening, including softening, ethylene production, and color development (Giovannoni, et al.), reduces the concentration of E4 mRNA by greater than 10-fold. The sequence of the E4 promoter has been published (Cordes, et al.) and the DNA sequence of the minus 1173 base pair region is presented in the first portion of FIG. 14.

The tomato E4 promoter may be employed in vector constructs used to produce transgenic plants, such as transgenic tomatoes. For example, a vector engineered according to methods of the present invention (detailed below), containing the tomato E4 promoter connected to the AdoMetase gene (e.g. vector pAG-5520), may be used to produce transgenic raspberries, strawberries, melons, carnations, cauliflower, and the like. The AdoMetase gene will be expressed in the fruit of these transgenic plants and will delay ripening. An advantage of this method is a savings of time and resources involved in vector construction, since the same vector can be used to transform many different plant types.

Alternatively, E4 promoter sequences may be isolated from the same type of plant that is to be transformed, and incorporated into the vector constructs used to perform the transformations. For example, a raspberry E4 promoter may be connected to a heterologous gene, such as the AdoMetase gene, and used to transform raspberries. This method is typically preferable, because a promoter from the same type of plant as is transformed is more likely to contain all of the regulatory elements required for appropriate stage and tissue specificity of expression. E4 promoters may isolated from other plants using a number of methods, including those described below.

B. Identification of Plant E4 Promoters

The present invention provides for the use E4 promoters from species other than tomato in vector constructs containing heterologous genes. Southern blot experiments performed in support of the present invention demonstrate the presence of DNA molecules having high sequence homology with the tomato E4 gene in raspberry, strawberry, melon, carnation and cauliflower. Similar Southern blot analyses may be performed on other fruit-bearing plants to identify additional E4 genes.

A Southern blot analysis used herein is detailed in Example 1. E4 homologues are identified in a Southern blot of the genomic DNA of the plants listed above probed with a labelled DNA fragment containing the coding sequence of the tomato E4 gene.

The probe is selected to contain the coding sequence of tomato E4, rather than the promoter sequence, because coding sequences are typically more conserved from species to species than are promoter sequences. In the experiments detailed in Example 1, probe molecules are generated from tomato genomic DNA using primer-specific amplification (Mullis; Mullis, et al.). The oligonucleotide primers are selected such that the amplified region included the entire coding sequence of the tomato E4 gene. Primers may also be selected to amplify only a selected region of the E4 gene.

Alternatively, a probe can be made by isolating restriction-digest fragments containing the sequence of interest from plasmid DNA.

The probe is labeled with a detectable moiety to enable subsequent identification of homologous target molecules. Exemplary labeling moieties include radioactive nucleotides, such as $^{32}$P-labeled nucleotides, digoxygenin-labeled nucleotides, biotinylated nucleotides, and the like, available from commercial sources.

In the case of primer-amplified probe, labeled nucleotides may be directly incorporated into the probe during the amplification process. Probe molecules derived from DNA that has already been isolated, such as restriction-digest fragments from plasmid DNA, are typically end-labeled (Ausubel, et al.).

Target molecules, such as HindIII DNA fragments from the genomes of the above-listed plants, are electrophoresed on a gel, blotted, and immobilized onto a nylon or nitrocellulose filter. Labeled probe molecules are then contacted with the target molecules under conditions favoring specific hybridization between the probe molecules and target molecules homologous to the probe molecules.

Conditions favoring specific hybridization are referred to as moderately to highly stringent, and are affected primarily by the salt concentration and temperature of the wash buffer (Ausubel, et al., Sambrook, et al.). Conditions such as those used in the final wash in Example 1 are typically classified as moderately stringent, due to the low salt concentration, and are expected to preserve only specific hybridization interactions, allowing the identification and isolation of homologous genes in different plant species.

Following contacting, hybridization, and washing, target molecules with sequences homologous to the probe are identified by detecting the label on the probe. The label may be detected directly, for example, as in radioactive label detected on autoradiograms, or it may be detected with a secondary moiety, for example, fluorescently-labeled streptavidin binding to a biotinylated probe.

C. Isolation of Other E4 Promoters

Following the identification of plants containing E4 genes, the DNA encoding the genes, including the promoter regions, may be isolated from the respective species, by, for example, screening a genomic DNA library. Experiments performed in support of the present invention, detailed in Example 2, demonstrate the isolation of a fragment of the raspberry E4 gene from a raspberry genomic DNA library.

The library of interest is screened with a probe containing sequences corresponding to the coding sequence of a known E4 gene, such as the tomato E4 gene. The screening is done using known methods (Ausubel, et al., Sambrook, et al.), essentially as described above.

Positive plaques or colonies are isolated, and the insert DNA is sequenced and compared to known E4 sequences. Clones containing inserts with sequences corresponding to genes homologous to tomato E4 are identified and, if necessary, used to obtain additional clones until the promoter region of interest is isolated.

III. Heterologous Genes

According to methods of the present invention, heterologous genes are linked to the promoters of the present invention. Exemplary heterologous genes for the transformation of plants includes genes whose products are effective to reduce ethylene biosynthesis in specific tissues of those plants, e.g. the fruits, flowers or leaves. One of these genes, AdoMetase, is discussed in detail below.

A. Ethylene Synthesis

Figure 2A:
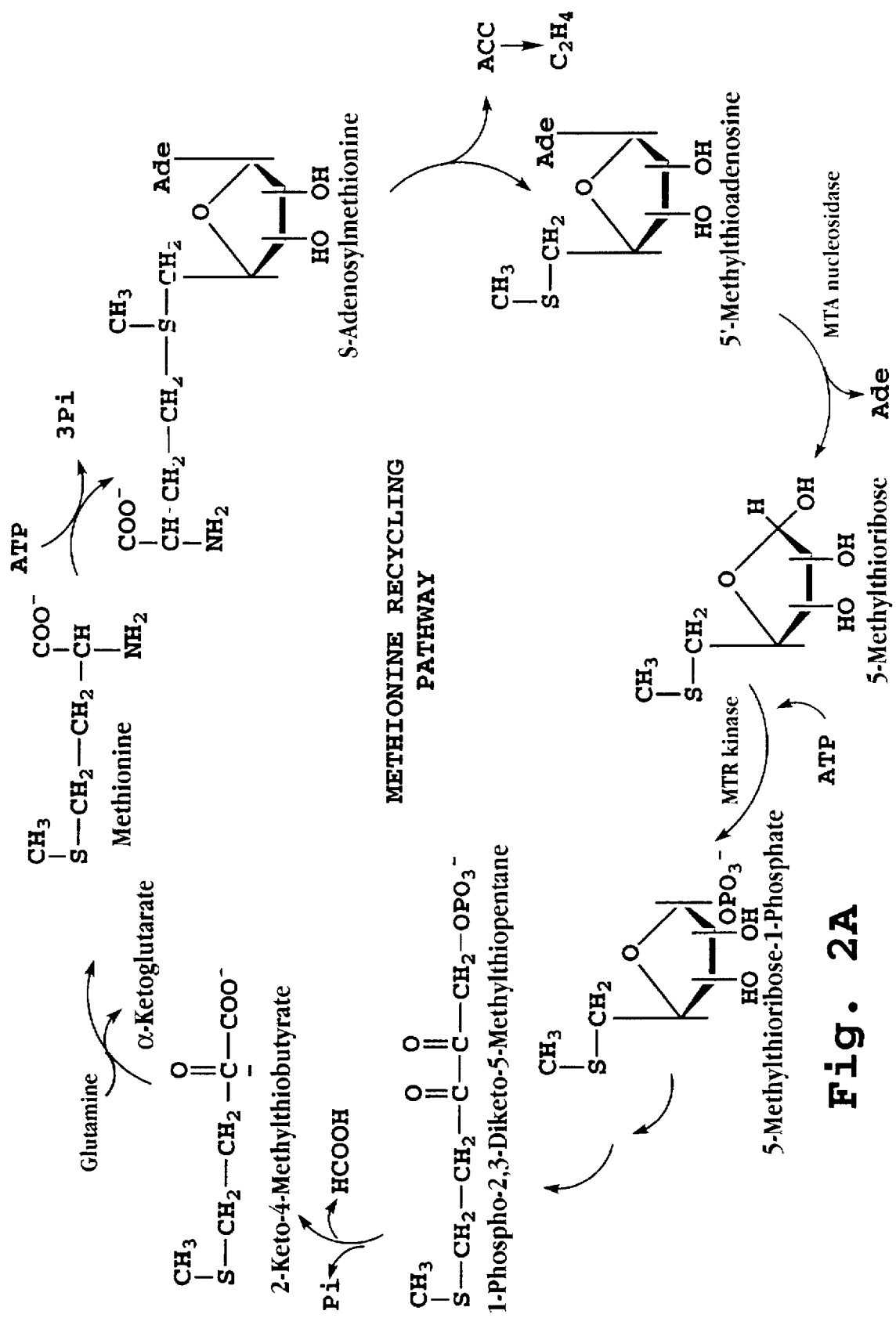
FIGS. 2A–2B schematically illustrates the metabolic reactions for the synthesis of ethylene from methionine under both normal and stress conditions.

The amino acid methionine has been shown to be a precursor of ethylene ($C_2H_4$) in plant tissues (reviewed by Imaseki). Methionine, however, is not the immediate precursor but first must be converted to the sulfonium compound S-adenosylmethionine (SAM) and, subsequently, aminocyclopropane-1-carboxylic acid (ACC) prior to conversion to ethylene. The metabolic reactions for the synthesis of ethylene from methionine under both normal and stress conditions are presented in FIG. 2A, and summarized as follows:

Methionine→SAM→ACC→Ethylene

ACC synthase catalyzes the degradation of SAM to ACC and 5'-methylthioadenosine (MTA). This enzymatic reaction appears to be the rate limiting step in ethylene formation. For example, the natural plant hormone indoleacetic acid (IAA or auxin) stimulates ethylene production by inducing the synthesis of ACC synthase. Conversely, the synthesis of SAM from methionine and the production of ethylene from ACC do not require auxin induction.

In addition, wounding and fruit ripening induces the formation of ACC synthase and, therefore, the conversion of SAM to ACC. The other product of the ACC synthase reaction, MTA, must be recycled back into methionine so as to provide an adequate supply of methionine for continual ethylene production. This recycling pathway from MTA to methionine, also presented in FIG. 2A, has been shown to exist in plant tissue (Adams, et al.; Kushad, et al.). The degradation of MTA has added significance in light of the finding that MTA is a potent inhibitor of ACC synthase. The importance of the degradation and recycling of MTA in normal plant tissues is, therefore, twofold: 1) to prevent the direct inhibition of ethylene synthesis by MTA, and 2) to provide adequate methionine for continual ethylene synthesis.

The first step in the degradation of MTA in plant tissue is the hydrolysis of this nucleoside to 5-methylthioribose (MTR) by a specific MTA nucleosidase. MTR not only provides its methylthio moiety for the formation of methionine, but also contributes four carbons from its ribose towards the synthesis of this amino acid. Therefore, the methylthio group is conserved by recycling. It should be noted that this pathway merely maintains a methionine supply for ethylene biosynthesis, but does not result in a net increase in methionine synthesis.

1. AdoMet hydrolase

The approach to reduce ethylene biosynthesis in plants reported here utilizes a gene that encodes the enzyme S-adenosylmethionine hydrolase (also described in a co-owned, co-pending file wrapper continuation of U.S. patent application Ser. No. 07/613,858, filed 12 Dec. 1990, now abandoned herein incorporated by reference and in U.S. application Ser. No. 08/046,583, filed 9 Apr. 1993, herein incorporated by reference). This enzyme, encoded by the E. coli bacteriophage T3, hydrolyses AdoMet to homoserine and MTA. The enzyme is known as its recommended name, AdoMet hydrolase (AdoMetase), or by its other name, S-adenosylmethionine cleaving enzyme (SAMase) (Studier, et al.). Both products of the reaction (i.e., homoserine and MTA) are recycled to methionine; MTA as previously shown (FIG. 2A) and homoserine via a metabolism pathway known to exist in plant tissues.

The AdoMetase gene has been identified, isolated, cloned, and sequenced (Hughes, et al., 1987a; Hughes, et al., 1987b). The gene contains two in-frame reading sequences that specify polypeptides of 17105 and 13978 daltons. Both polypeptides terminate at the same ochre codon. This results in the 14 kd polypeptide being identical to 82% of the 17 kd polypeptide starting at the carboxyl end of the longer polypeptide. Both polypeptides are present in partially purified cells and from E. coli expressing the cloned gene (Hughes, et al., 1987b; Studier, et al., 1976). Other bacteriophages that encode the AdoMetase or SAMase genes are coliphage BA14, Klebsiella phage K11, and Serratia phage IV (Mertens, et al.; Horsten, et al.).

Figure 2B:
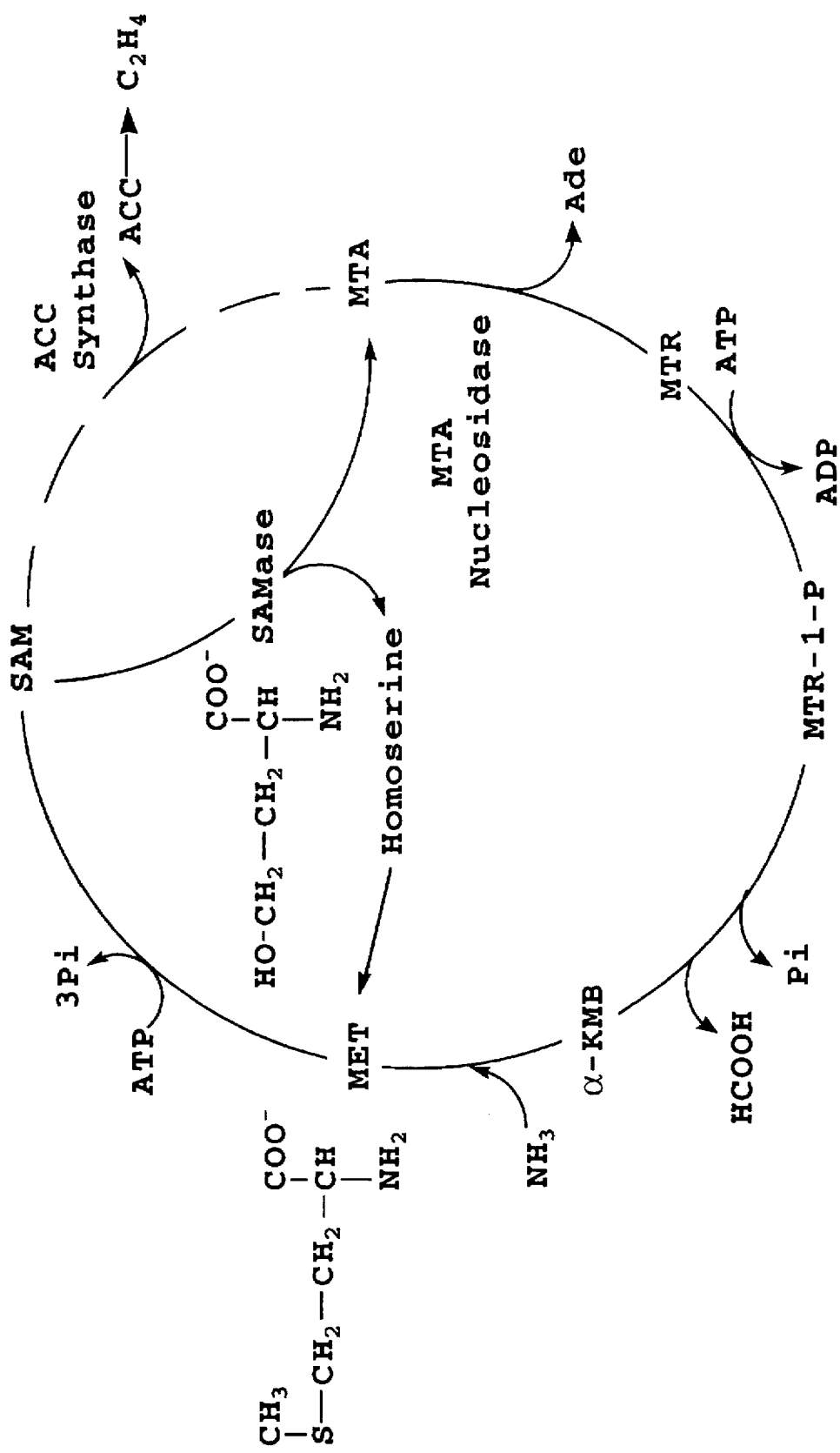

The effect AdoMetase expression in plant cells has on the plant methionine recycling pathway is shown schematically in FIG. 2B. Experiments performed in support of the present invention, using transgenic tomatoes expressing an AdoMetase gene and monitoring ethylene production, have demonstrated that the effect of AdoMetase on the pathway is to "short circuit" the branch that produces ethylene: ethylene production is reduced in such transgenic plants.

Different bacteriophages may be expected to contain AdoMetase genes with variations in their DNA sequences. The isolation of AdoMetase coding sequences from bacteriophage coding sequences can be accomplished as previously described for AdoMetase from bacteriophage T3. Alternatively, degenerative hybridization probes for AdoMetase coding sequences can be generated and used to screen plasmids carrying fragments of a selected bacteriophage's genome for the presence of homologous sequences. AdoMetase enzymatic activity can be evaluated by standard biochemical tests (see for example, Example 8).

Furthermore, the amino acid sequence of AdoMetase may be modified by genetic techniques to produce enzymes with altered biological activities (see below). An increase in the biological activity could permit the use of lower amounts of the enzyme to control ethylene biosynthesis in plants.

IV. Vector Construction

Plant transformation vectors are constructed according to methods known in the art (see, for example, Houck, et al., and Becker, et al.)

Figure 3:
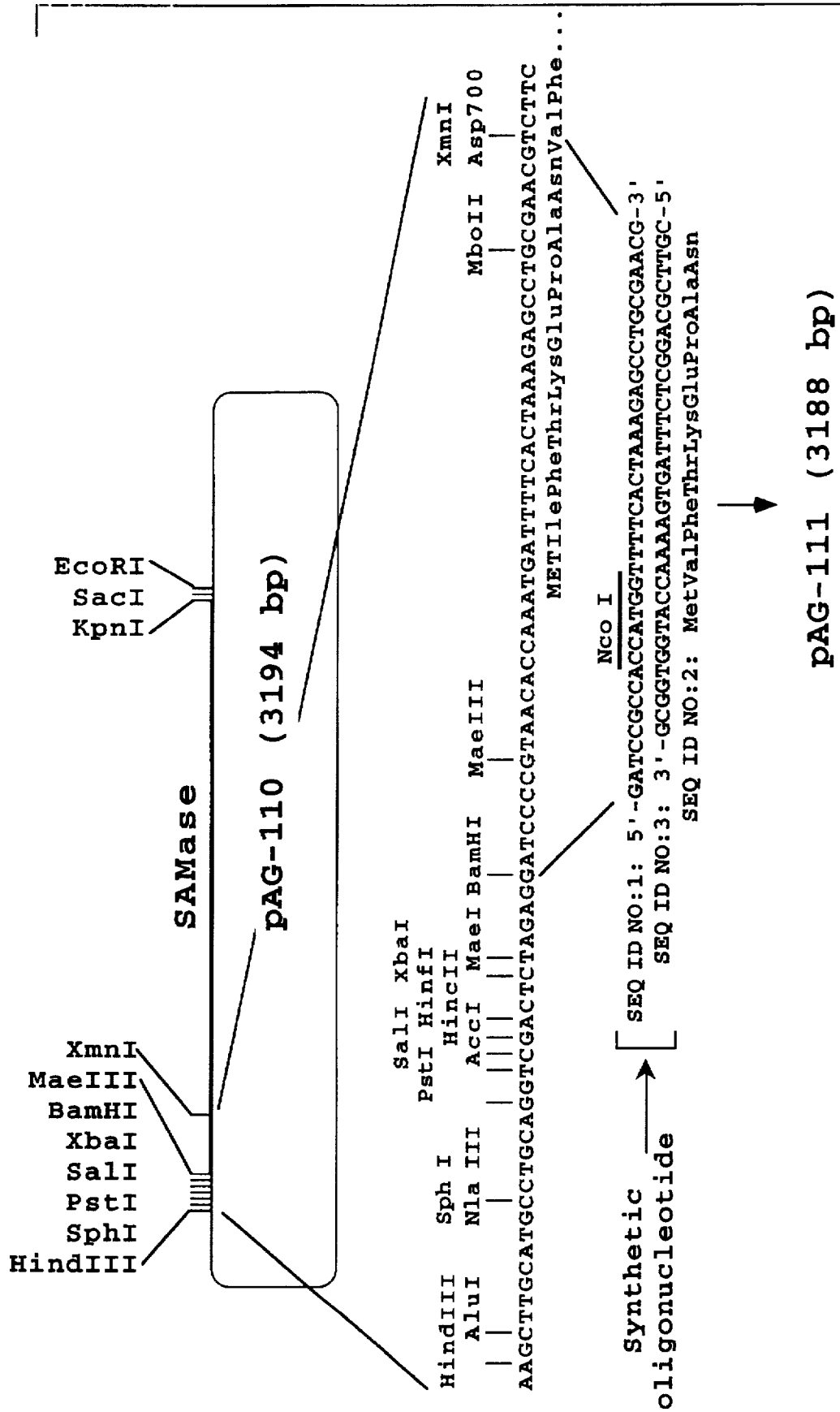
FIG. 3 outlines the steps followed in constructing vector pAG-111.

A series of recombinant DNA manipulations are performed in the AdoMetase gene prior to placement in an Agrobacterium expression vector. Initially, a MaeIII to BamHI fragment from M13HB1 (Hughes, et al., 1987a) is subcloned into the pUC19 plasmid vector to produce pAG-110 (FIG. 3). To increase the translational efficiency of the AdoMetase gene in plants, site directed mutagenesis of the nucleic acid sequences surrounding the ATG start codon is performed. A synthetic double stranded 39 base pair oligonucleotide is synthesized and substituted for the BamHI to XmnI fragment at the 5' end of the gene (FIG. 3). The net effect of this substitution is to change the CACCAAATGA (SEQ ID NO:14) in the native T3 sequence to GCCACCATGG (SEQ ID NO:15) which is an optimal eukaryotic translational initiation sequence (Kozak, et al.; Lutcke, et al.).

The change also introduces an NcoI site (CCATGG) at the AdoMetase start codon which facilitates fusions to different promoters. The only alteration to the AdoMetase coding sequence is the amino acid at amino acid position two which is changed from isoleucine to valine: this is a highly conservative amino acid change.

Experiments performed in support of the present invention have demonstrated constitutive expression of AdoMetase in transgenic tomato plants. In these plants there is a significant reduction in the ability of these plants to synthesize ethylene.

Figure 5A:
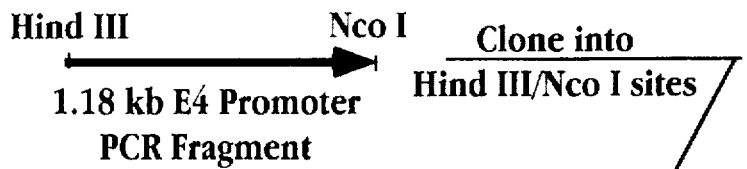
FIGS. 5A–D show a diagram of the steps followed in constructing vectors pAG-111 (FIGS. 5A–5B), pAG-117 (FIGS. 5B–5C) and pAG-5520 (FIGS. 5C–5D).
Figure 5B:
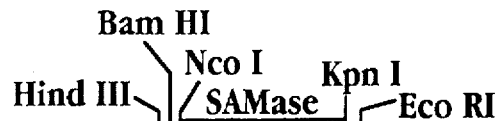
Figure 5C:
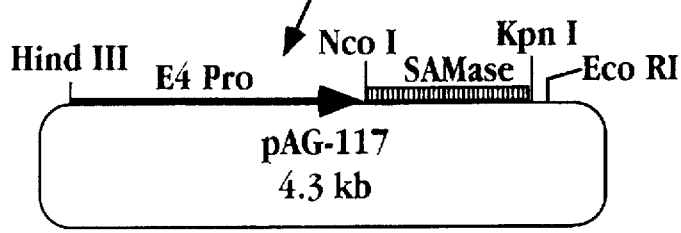

Using the sequence shown in FIG. 13 primers are prepared for use in the polymerase chain reaction (PCR) to amplify a 1177 base pair region of the E4 promoter from tomato genomic DNA (Example 3). The primers are designed with unique restriction sites at each end and were used to place the promoter in the proper orientation 5' of the SAMase gene in pAG-111 (FIGS. 5A, 5B). The 5' end of the promoter fragment has a HindIII site, while the 3' end has an NcoI site (CCATGG) placed such that the ATG start codon of the E4 gene product is used as the ATG in the NcoI site. This allows precise placement of the entire E4 promoter directly in front of the SAMase amino acid coding sequences with no intervening sequences (Example 3. FIGS. 5C and 14(2)).

A selectable vector expressing AdoMetase under the control of the E4 promoter (pAG-5520) is constructed as detailed in Example 3 and schematized in FIGS. 5A–5D. For selection, the vector contains the neomycin phosphotransferase II gene, providing aminoglycoside antibiotic (e.g. kanamycin) resistance.

V. Plant Transformation

A. Methods of Transforming Plants pAG-5520 is transferred to tomato plants (Example 4) to generate transgenic plants expressing AdoMetase. Tomato progenitor cells (tomato cotyledon tissue explants) are transformed with EHA101 bacteria containing pAG-5520 and grown in tissue culture in the presence of kanamycin for 8 to 10 weeks to produce plants.

A number of methods, in addition to Agrobacterium-based methods, may be employed to elicit transformation of plant progenitor cells, such as electroporation, microinjection, and microprojectile bombardment. These methods are well known in the art (Comai, et al., Klein, et al.; Miki, et al.; Bellini, et al.) and provide the means to introduce selected DNA into plant genomes: such DNA may include a DNA cassette which consists of the E4 gene promoter functionally adjacent, for example, AdoMetase coding sequences.

B. Identifying and Evaluating Transformants

Several transgenic plants are assayed for their ability to synthesize AdoMetase mRNA, AdoMetase protein, and their ability to inhibit the biosynthesis of ethylene. The assays are performed after the plant tissue being assayed has been subjected to a wound, and are carried out both on leaves of the plant, as well as the fruit. Leaf wounds are typically cuts on the leaf, performed either with a dull knife or with a circular bore. Fruit "wounds" can be as mild as picking the fruit from the plant.

Leaf-based assays can be informative if the promoter driving the heterologous gene (transgene) is at least somewhat active in leaf tissue, as is the case for the E4 promoter. In such cases, leaf-based assays are useful for initial screens of the expression level of a transgene, since they can be performed much earlier than fruit-based assays. Fruit-based assays, on the other hand, provide more accurate data on transgene expression in the target tissue itself (fruit). The results of both types of assays are detailed in Example 8.

Figure 7A:
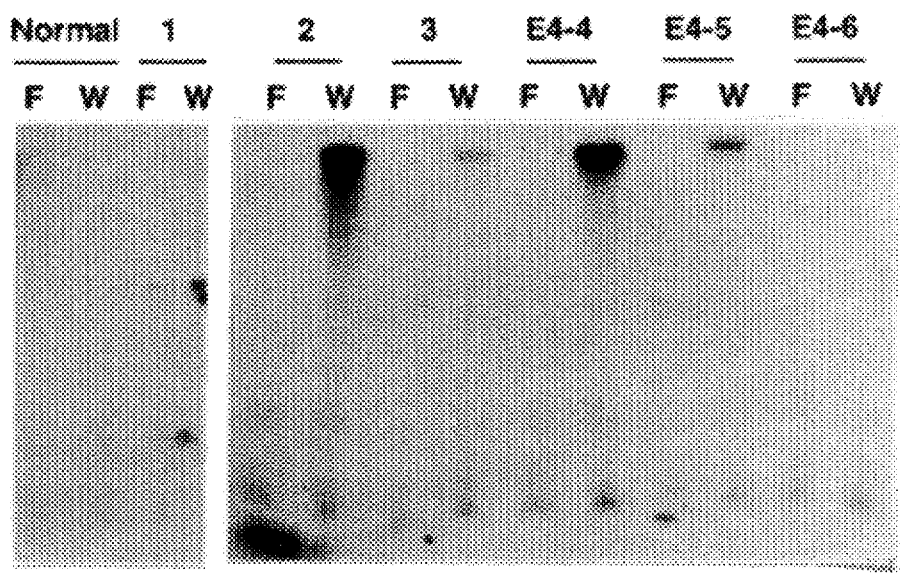
FIGS. 7A and 7B show a the results of an RNAse protection assay to detect SAMase mRNA in fresh and wounded leaves of normal and E4/SAMase transgenic tomato plants.
Figure 7B:
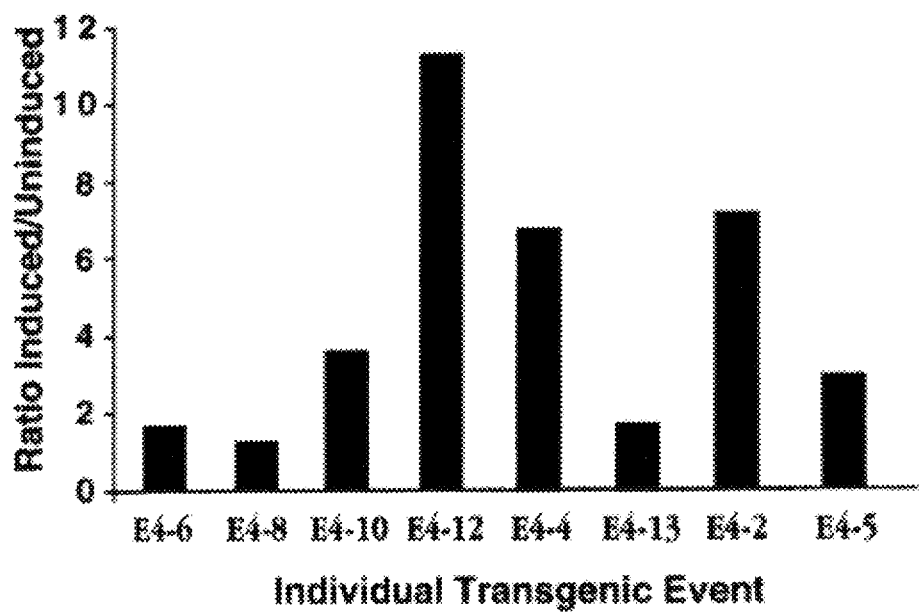
Figure 9:
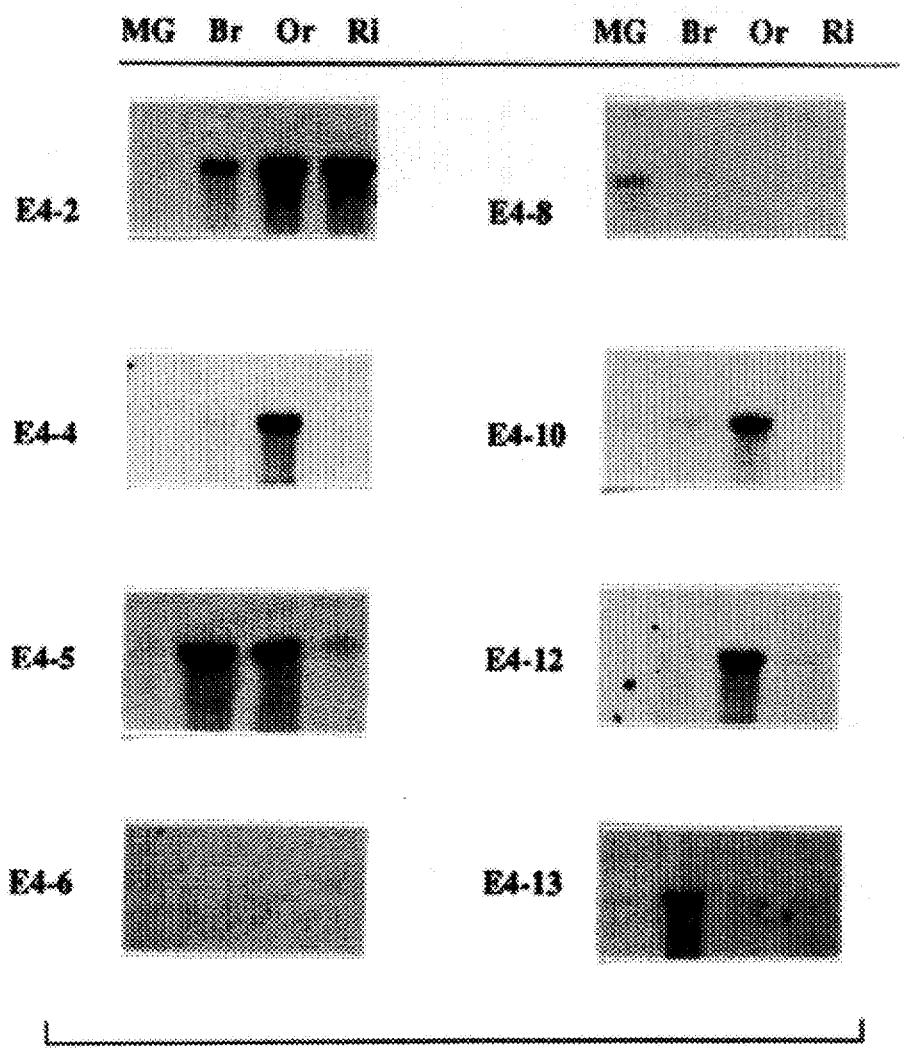
FIGS. 9 and 10 show the results of an RNAse protection assay to detect SAMase mRNA in E4/SAMase transgenic tomato ripening fruit at four stages of ripening.
Figure 10:
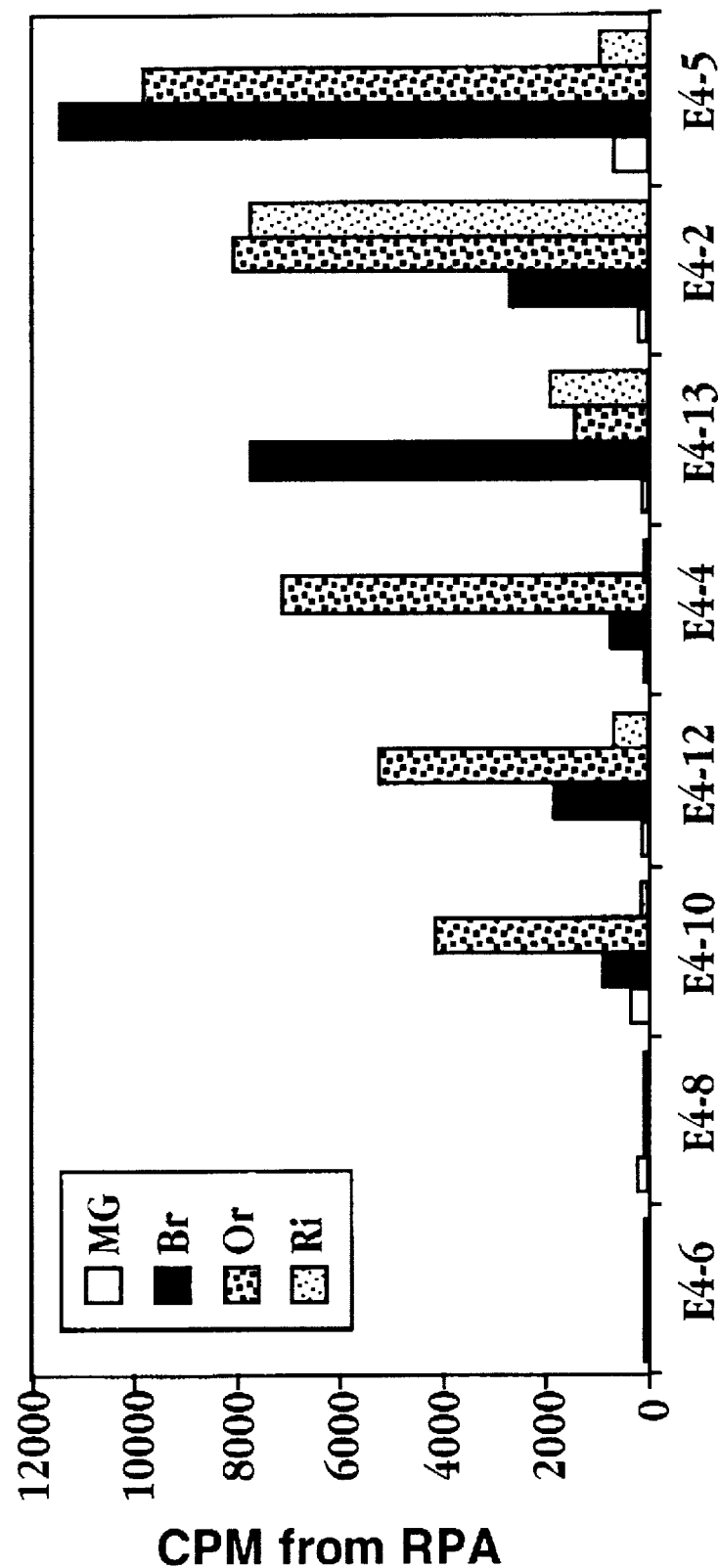

AdoMetase mRNA levels are determined using, for example, an RNAase protection assay (RPA) (Example 5). FIGS. 7A and 7B show the results of an RPA using fresh or wounded leaves from normal and transformed tomato plants. Plants showing detectable transgene mRNA expression in leaves are grown to produce fruit, and the fruit is then tested mRNA expression. FIGS. 9 and 10 shows the results of an RPA using the fruit from one transgenic plant at different stages of fruit ripening. While the absolute level of expression varies considerably among different transformed lines, the relative level of expression as a function of ripening stage is consistently transient, typically peaking at the orange stage, with expression at low levels in fully ripe fruit in all but one case.

Figure 8:
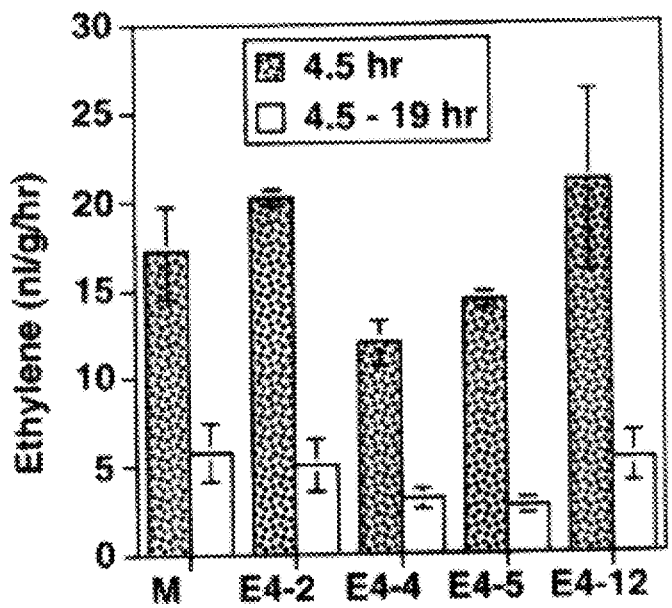
FIG. 8 shows a bar graph of ethylene production in wounded leaves of normal and E4/SAMase transgenic tomato plants.

Ethylene biosynthesis is measured in leaves and fruit of transgenic tomatoes. FIG. 8 shows the level of ethylene synthesis in wounded leaves from normal (M) and four transgenic tomato plants. The experiments are performed as detailed in Example 6. Some of lines show a reduction in ethylene biosynthesis, but the values are not well correlated with those obtained in the RNAse assay presented in FIGS. 7A and 7B. The assay is nevertheless useful for screening, as suggested above, since plants negative for AdoMetase expression in leaf wound assays are also negative for AdoMetase expression in fruit.

Figure 12:
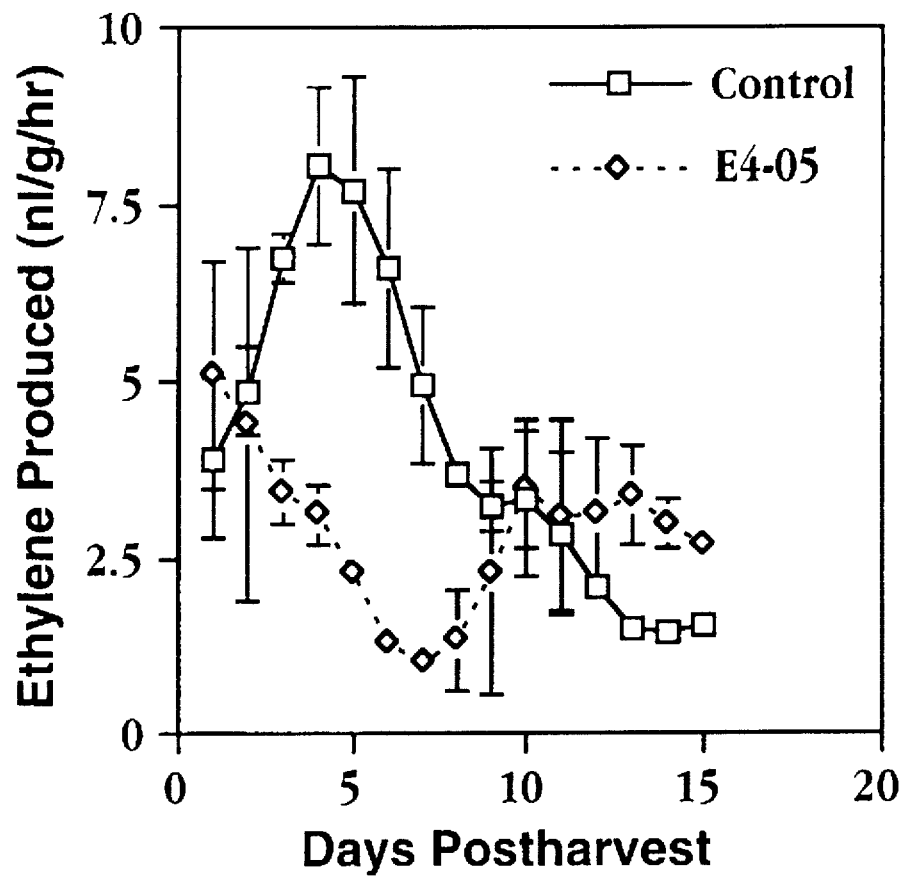
FIG. 12 shows a chart of ethylene production in normal and E4/SAMase transgenic tomatoes as a function of time after harvest.

Ethylene biosynthesis in transgenic fruit, is typically reduced relative to control fruit, as is shown in FIG. 12. Whereas control tomatoes show an increasing rate of ethylene synthesis during the 5 days following harvest, fruit from transgenic line E4-05 shows a decreasing rate of synthesis, which bottoms out approximately one week post-harvest. This result demonstrates that constructs of the present invention are effective at reducing the level of ethylene biosynthesis in the fruit of fruit-bearing plants.

After these timepoints, the rates of ethylene synthesis reverse directions for both normal and transgenic plants. This characteristic demonstrates the physiological effects of the transient nature of heterologous gene expression under control of an E4 promoter, and that activation of the E4 promoter, for example, by wounding, can transiently inhibit ethylene biosynthesis.

Figure 11:
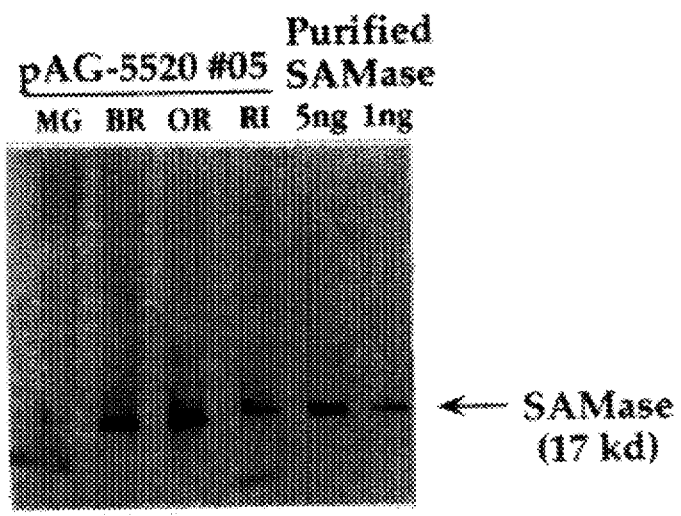
FIG. 11 shows the results of a Western blot, of E4/SAMase transgenic tomatoes at four stages of ripening, probed with an antibody to SAMase.

To correlate the effects of AdoMetase mRNA expression, Western Blots were performed,as detailed in Examples 7 and 8. The results are shown in FIG. 11. These results demonstrate that transformation of tomato progenitor cells with a construct containing the E4 promoter coupled to the AdoMetase gene is effective to reduce ethylene biosynthesis in the fruit of the transgenic plants, and further, that this reduction can have a transient timecourse.

The biological effects of AdoMetase gene expression include a cessation of color development beyond the light red stage, and tomatoes that remain firm much longer than untransformed controls.

VI. Advantages of the Invention

These results demonstrate the ability to provide tissue specific regulation to the AdoMetase enzyme in transgenic plants. In addition, the results obtained with the E4 promoter suggest the use of this promoters for similar tissue specific expression of any desired gene product. A tissue or stage specific promoter is a region of DNA that regulates transcription of the immediately adjacent (downstream) gene to a specific plant tissue or developmental stage of the plant or plant tissue. Other gene products which may be useful to express using these promoters include genes encoding (i) flavor or color modification proteins, (ii) enzymes, such as is encoded by the taumatin gene, that modify lycopene synthesis, and (iii) gene products that affect ethylene production, such as antisense or enzymes. Further, it is useful to restrict expression of some genes to specific tissues, such as the fruit—for example, any gene that would be deleterious to the plant if it were expressed constitutively. Such genes would include genes which encoded degradative enzymes that deplete necessary metabolites. As can be seen from the results described above, derivatives of the E4 promoter region can be used as on/off switches for the tissue and stage specific expression of genes whose expression is under their control.

The present method is applicable to all higher plants. A reporter gene, such as GUS (β-glucuronidase), can be used to test tissue specific regulatable expression from this promoter. Expression of GUS protein can be easily measured by fluorometric, spectrophotometric or histochemical assays (Jefferson, 1987).

Variants of the E4 promoter may be isolated from different tomato cultivars and from other plants by the methods described above.

VII. Utility

The present invention has several utilities. Experiments performed in support of the present invention demonstrate that tomatoes transformed with an AdoMetase gene under the control of a tomato E4 promoter exhibit significantly lower levels of ethylene production following harvest. Due to the deleterious effects of ethylene biosynthesis on the handling and storage of commercially-important plants and plant products, such as tomatoes, detailed above, plants in which ethylene synthesis is reduced are of substantial value.

For example, because transgenic tomatoes of the present invention remain firm much longer after harvest than normal tomatoes, such transgenic tomatoes may be harvested at a later, vine-ripened, stage and still retain the transportability previously associated with, for example, green tomatoes.

Similarly, flowering plants containing heterologous genes effective to reduce ethylene biosynthesis will retain a fresh appearance longer than untransformed counterparts. Reduced ethylene biosynthesis in leafy vegetables, such as lettuce, would reduce leaf browning and lead to a longer shelf-life.

The following examples illustrate, but in no way are intended to limit the present invention.

Materials and Methods

Tomato seed (*Lycopersicon esculentum* Mill. var. *cerasiforme* (Dunal) Alef. cv. Large Red Cherry) were obtained from Peto Seed, Inc. (Saticoy, Calif.) and were grown under standard greenhouse conditions. Harvested fruit were stored at room temperature (22° C.).

Standard recombinant DNA techniques were employed in all constructions (Adams, et al.; Ausubel, et al., Sambrook, et al.).

EXAMPLE 1

Southern Blot Analysis of E4 Homologues in Several Species of Plants

A Southern blot analysis was conducted to determine if sequences homologous to the tomato E4 gene were present in other plant species. The blot consisted of HindIII digests of six genomic plant DNAs: tomato, raspberry, strawberry, melon, carnation and cauliflower, along with size standards. This blot was hybridized with a probe following standard methods (Maniatis, et al.). The probe was a ~740 bp polymerase chain reaction (PCR; Mullis; Mullis, et al.) product amplified from genomic tomato DNA using PCR primers flanking the coding sequence of the E4 gene. The probe was labeled by incorporating $^{32}$P-labeled nucleotides into the PCR reaction.

The primers were designed according to Cordes, et al. (1989). The 5' primer sequence, corresponding to the region between nucleotides 1439 and 1452 of the E4 gene (SEQ ID NO:8), is represented as SEQ ID NO:6 (ACG CAT GGA GGG TAA CAA). Positions 5-7 of this primer correspond to the ATG start codon of the E4 gene. The 3' primer sequence, corresponding to the region between nucleotides 2160 and 2177 of the E4 gene (SEQ ID NO:8), is represented as SEQ ID NO:7 (GAA GCA AGA CAG CAA ATG).

An autoradiograph of the blot is shown in FIG. 1. Several bands are apparent in each lane, with the lane corresponding to tomato DNA showing the strongest signal.

EXAMPLE 2

Isolation of DNA Fragments Homologous to Tomato E4 from a Raspberry Genomic Library A. Screening of the Library.

A raspberry genomic library in lambda GEM-11 was obtained from Novagen (Madison, Wis.) and screened by standard methods with the tomato E4 gene probe described above. Three lambda clones which hybridized to the probe were identified. The clones were purified by 3 rounds of plaque purification. One of the clones was selected for further analysis.

B. Analysis of a Positive Clone.

The clone was digested with several enzymes (Apa I, Bam HI, Eco RI, Hind III, Nco I, Sac I, and Sal I), run on a gel, and transferred to a "SUREBLOT" nylon membrane (Oncor, Gaithersburg, Md.). The blot was hybridized overnight at 42° C. with the tomato E4 probe in "HYBRISOL I" hybridization cocktail (Oncor, Gaithersburg, Md.). The final (most stringent) wash was 0.1% SSC, 0.1% SDS for 30 minutes at room temperature (22° C.).

A 1.6 kb Sac I fragment which hybridized to the probe was subcloned into pGEM5Zf(+) (Promega, Madison, Wis.) and further characterized. A 225 bp region in that fragment was found to be highly homologous to the tomato E4 gene at both the DNA level (74%) and the amino acid level (80%). The sequence of this region (SEQ ID NO:12) is compared to the sequence of a portion of the tomato E4 gene (SEQ ID NO:8) in FIG. 15.

EXAMPLE 3

Cloning of the AdoMetase Gene

A. Isolation of the AdoMetase Gene.

The AdoMetase (SAMase) gene was identified on an AluI-HaeIII restriction fragment from purified T3 DNA (Hughes, et al., 1987a). Bacteriophage T3 is available under ATCC No. 11303-B3 (American Type Culture Collection, 12301 Parklawn Dr., Rockville Md. 20852). The DNA fragment was first cloned into the bacteriophage M13 MP8 vector (Pharmacia LKB Biotechnology, Inc., Pistcataway, N.J.). A MaeIII to BamHI fragment was subcloned into the pUC19 plasmid vector (Pharmacia) to produce pAG-110 (FIG. 1). This vector was transformed into *E. coli* and used as a source of DNA for further construction experiments, detailed below.

B. Modification of the Amino-Terminal Sequence of the Cloned AdoMetase Gene.

The cloned AdoMetase gene was further engineered to contain a consensus eukaryotic translation initiation site (Kozak; Lutcke, et al.) by altering the nucleotide sequence surrounding the AdoMetase ATG start-codon using a synthetic double-stranded oligonucleotide.

Plasmid pAG-110 was digested with XmnI and BamHI and the 1.9 kb and 1.3 kb fragments were purified by electro-elution after agarose gel electrophoresis. A double stranded synthetic oligonucleotide linker formed by annealing oligonucleotides represented by SEQ ID NO:1 and SEQ ID NO:3 (FIG. 3) was ligated to the 1.9 kb fragment. This ligated DNA was subjected to XmnI digestion to remove excess linkers.

The linkered 1.9 kb fragment was then re-purified by electrophoresis on low melting temperature agarose and ligated to the 1.3 kb fragment to form the plasmid pAG-111. The altered gene region was sequenced to confirm its identity. pAG-111 was used in subsequent recombinant DNA manipulations, including the construction of plant expression vectors, detailed below. This plasmid DNA can also be used to directly transform the plant host via electroporation, microinjection, or microprojectile bombardment.

C. Vector Constructions using the Tomato E4 Promoter. 1. pAG-110 pAG-111, PAG-117

Figure 4:
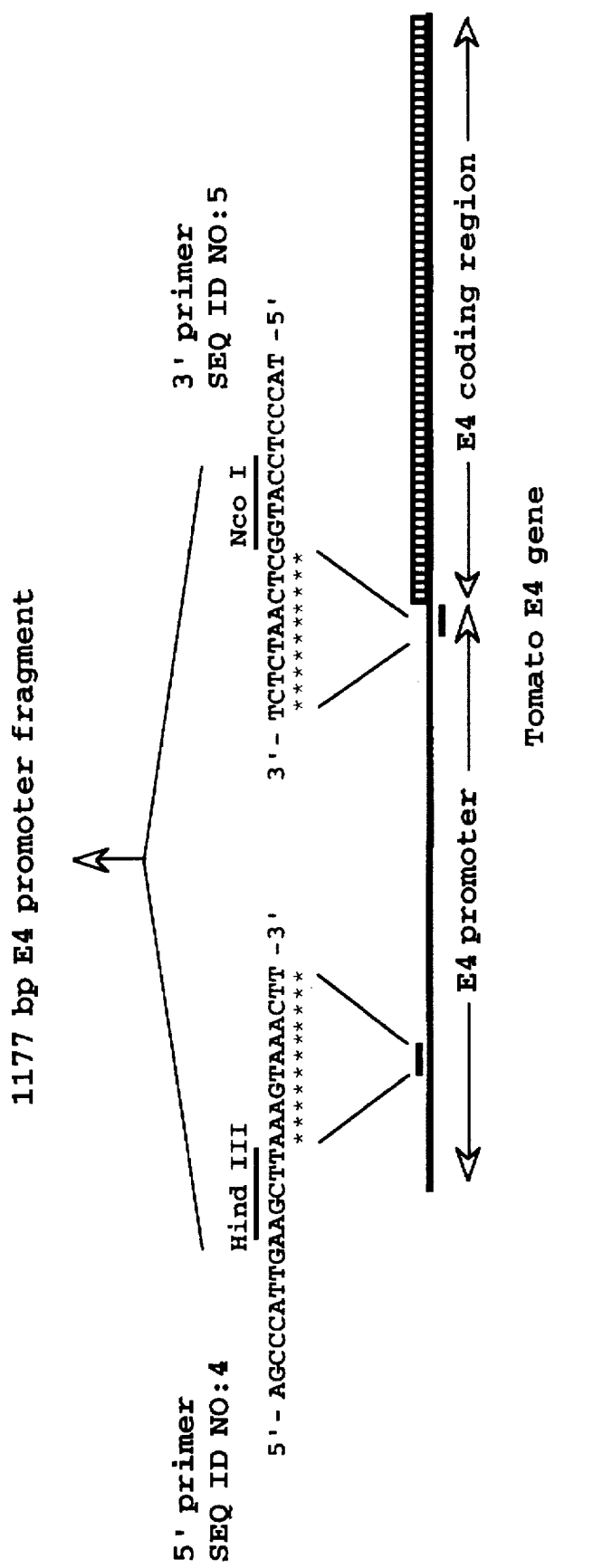
FIG. 4 shows a schematic of the tomato E4 gene, and the primers used to isolate a 1.18 kb tomato E4 promoter fragment.

A 1.18 kb E4 promoter was isolated from tomato (*Lycopersicon esculentum* var. *cerasiform*) DNA using the polymerase chain reaction (PCR; Mullis; Mullis, et al.; Perkin-Elmer Cetus, Norwalk Conn.). The primers used in the PCR reaction were based on the sequence described by Cordes, et al. The sequences of the 5' and 3' oligonucleotide primers, shown in FIG. 4, are represented as SEQ ID NO:4 and SEQ ID NO:5, respectively. The oligonucleotides were designed to incorporate restriction endonuclease sites (HindIII and NcoI) at the 5' and 3' ends, respectively, of the amplified E4-promoter fragment. These restriction endonuclease cleavage sites were used to subclone the E4-promoter fragment (FIG. 5A) into the pAG-111 vector (FIG. 5B), which contains an NcoI site at the ATG start codon in the region modified by the synthetic oligonucleotide (see FIG. 3). The resulting vector, containing an E4:SAMase chimeric construct in the region between the HindIII/KpnI sites, was termed pAG-117.

2. pAG-5321

Agrobacterium binary vectors were developed from pGA482 (An, et al., 1985), a pBIN19 derivative (Clontech Laboratories) containing the neomycin phosphotransferase II gene (providing kanamycin resistance) fused to the nopaline synthesis (NOS) gene promoter (An, et al., 1988).

Figure 6A:
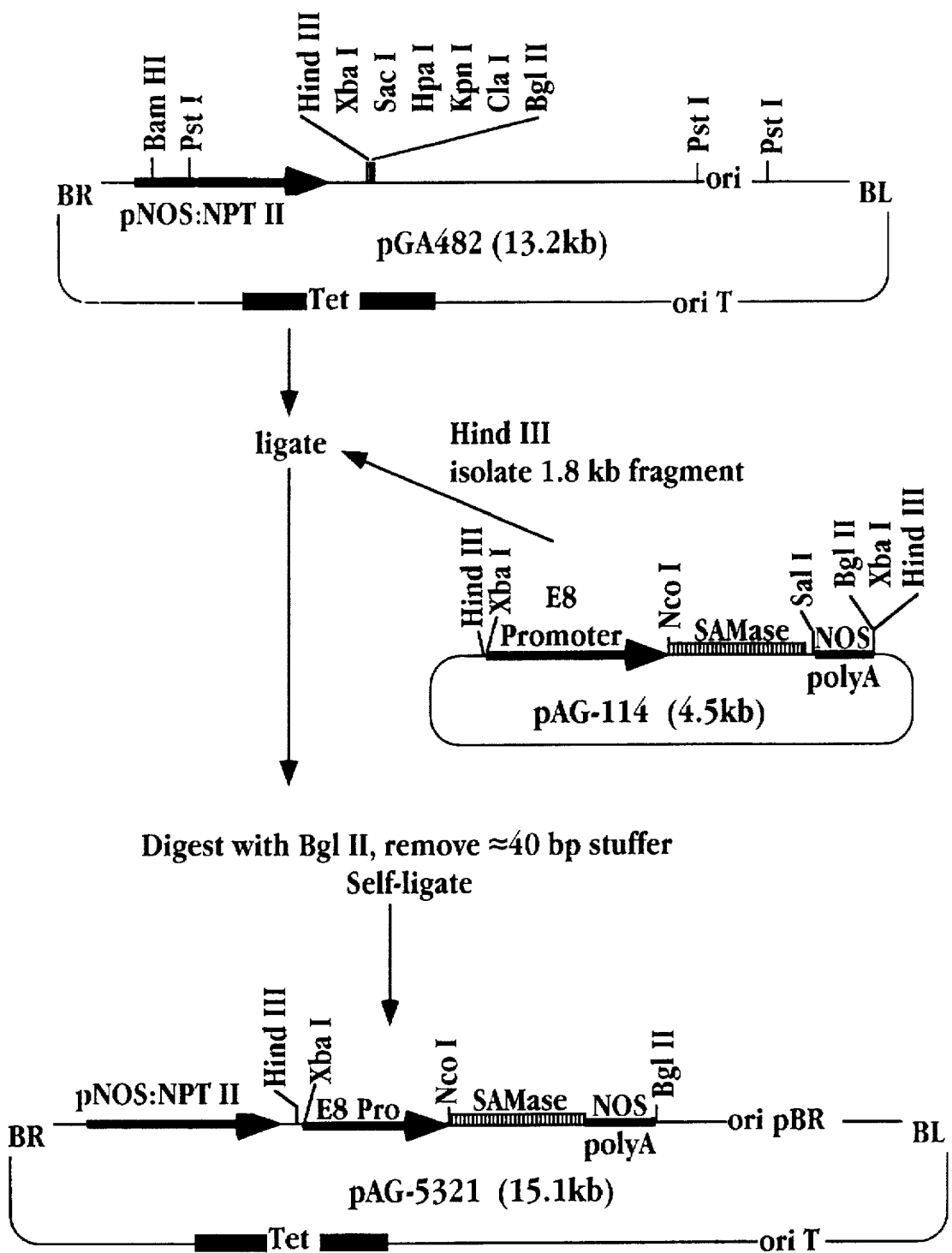
FIG. 6A shows a diagram of the steps followed in constructing vector pAG-5321.
Figure 6B:
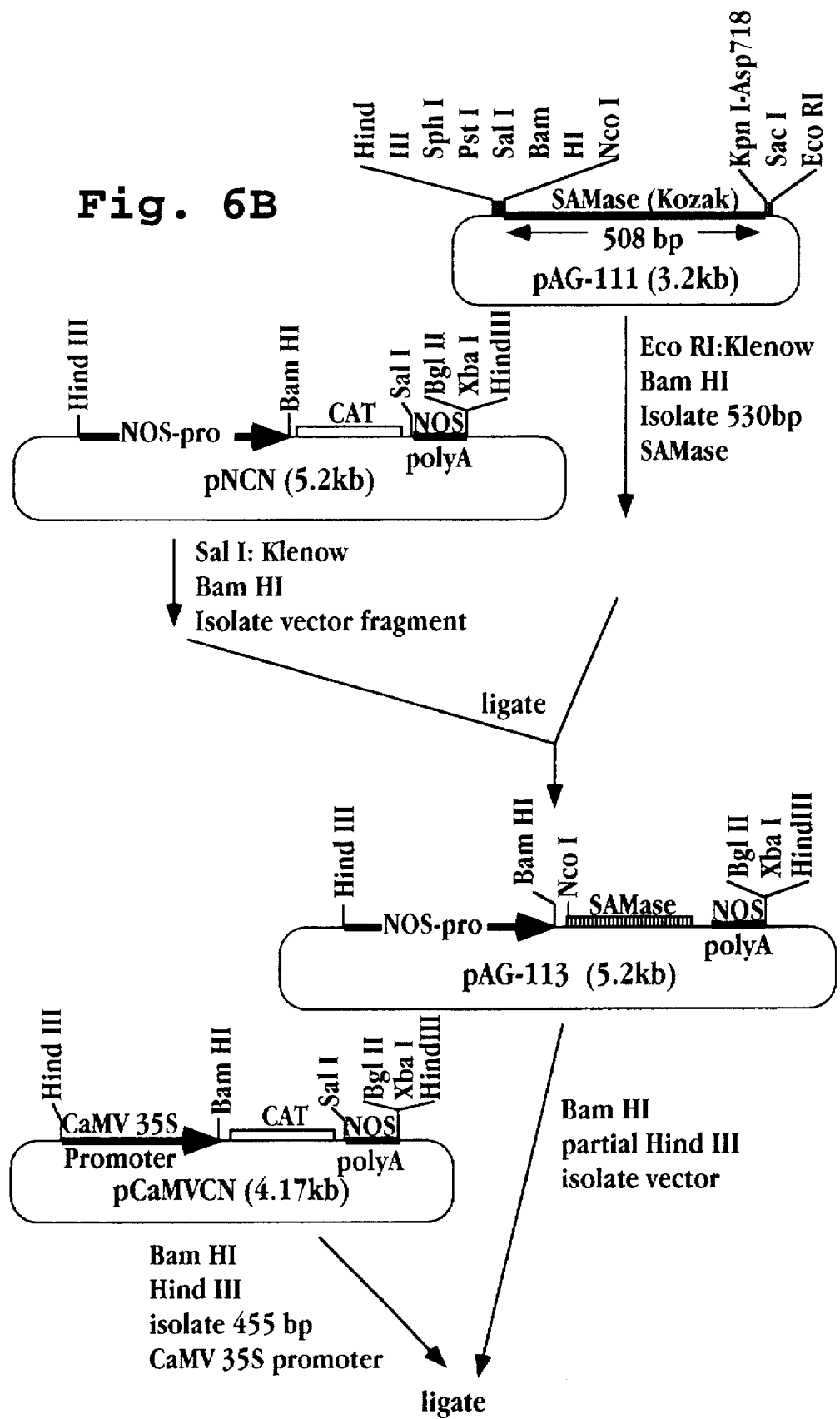
FIG. 6B shows a diagram of the steps followed in constructing vector pAG-114.
Figure 6C:
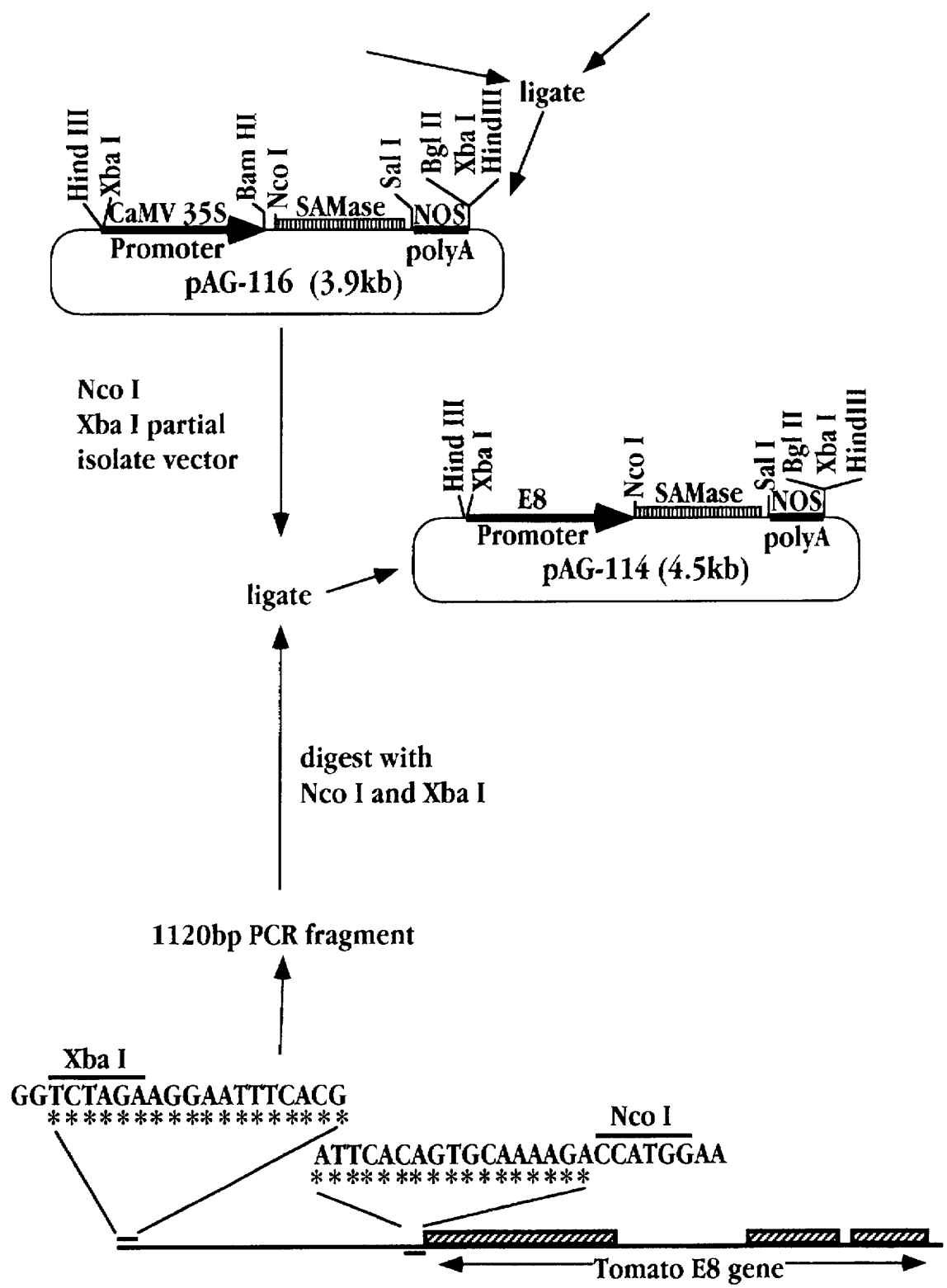

FIG. 6A outlines the generation of vector pAG-5321 starting from vectors pGA482 and pAG-114. FIG. 6B outlines the generation of the vector pAG-114 from vectors pAG-111 (described above) and pNCN (Pharmacia, Inc., Piscataway, N.J.).

3. pAG-5520

Figure 5D:
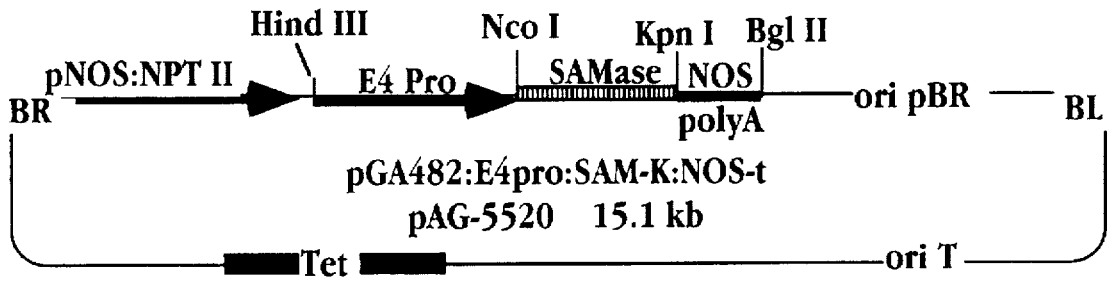

The E4: SAMase chimera was excised from pAG-117 with a HindIII/KpnI digest. The resulting 1.7 kb fragment was purified as above, and cloned upstream of the nopaline synthase polyA addition site in pAG-5321, resulting in pAG-5520 (FIG. 5D). The identity of the HindIII/KpnI insert was confirmed by DNA sequence analysis. This vector was used to generate the transgenic plants described herein.

FIGS. 5A–D and 6A–B outline one approach to the generation of Agrobacterium vectors for use in the present invention. However, the E4/SAMase cassette, present in, for example, pAG-117, can be incorporated in a number of vectors useful for plant transformation, such as pBI121 (Clontech Laboratories, Inc., Palo Alto, Calif.).

4. pAG-924

Vector pAG-924 was constructed by cloning the BamHI/KpnI SAMase fragment from pAG-111 into the same sites of pGEM7Zf(+) (Promega, Inc., Madison, Wis.). This plasmid was used to make the RNA probe for RNase protection assays, described in Example 3.

5. Other Constructs

DNA constructs may be made using genes other than the AdoMetase gene under the control of an E4 promoter, for example, other genes effective to reduce ethylene biosynthesis. Preferably, the E4 promoter is isolated from the same species of plant into which the construct is being introduced. For example, a tomato E4 promoter may be used to direct the expression of a heterologous gene, such as AdoMetase, in tomatoes, while a raspberry E4 promoter may be used to direct the expression of a heterologous gene in raspberries.

EXAMPLE 4

Plant Transformation

*Agrobacterium tumefaciens* strain EHA101 (Hood, et al.), a disarmed derivative of *Agrobacterium tumefaciens* strain C58, was used to introduce coding sequences into plants. This strain contains a T-DNA-less Ti plasmid. The pAG-5520 construct was transferred into EHA101 using electroporation essentially as described by Nagel, et al. Briefly, an *Agrobacterium tumefaciens* culture was grown to mid-log phase (OD 600 0.5 to 1.0) in MG/L media (5 gm tryptone, 2.5 g yeast extract, 5 gm NaCl, 5 gm mannitol, 1.17 gm sodium glutamate, 0.25 gm $K_2HPO_4$, 0.1 9 $MgSO_4$, 2 µg biotin per liter, pH adjusted to 7.2 with NaOH). After chilling on ice 250 ml of the culture were pelleted, resuspended in sterile, chilled 1 mM Hepes/KOH pH 7.0, pelleted and resuspended as before, pelleted again, resuspended in sterile, chilled 10% glycerol, pelleted again, resuspended in 500 µl sterile, chilled 10% glycerol and split into 80 µl aliquots which were frozen on dry ice/ethanol and stored at −800° C.

Typically, 0.1–1 µg of plasmid DNA was added to a 40 µl aliquot of cells and incubated on ice 30–60 seconds. The mix was then transferred to a 0.1 cm gap electroporation cuvette (Invitrogen) and pulsed at 1.25 kV (BioRad Gene Pulser at 25 µF, BioRad Pulse controller at 200Ω). One ml of MG/L media was added quickly after the pulse. The mixture was transferred to a microfuge tube and allowed to incubate at 28° C. for 1 hour. The cells were diluted 1:100, and 10 and 100 µl were plated on two MG/L plates containing 20 µg/ml kanamycin, respectively. Kanamycin-resistant transformed colonies appeared within 2 days.

Seven to eight day-old tomato cotyledon tissue explants were excised from both the tip and base of the cotyledon. Cotyledon explants were pre-conditioned for 2 days on tobacco feeder plates (Fillatti, et al.). The pre-conditioned explants were inoculated with EHA101 containing the pAG-5520 plasmid and placed in a 10 ml overnight culture of EHA101/pAG-5520 for 5 minutes. The explants were then co-cultivated with the EHA101 strain for 2 days on tobacco feeder plates as described by Fillatti, et al.

The explants were grown in tissue culture media (Fillatti, et al.) containing 2Z media, MS salts, Nitsch and Nitsch vitamins, 3% sucrose, 2 mg/l seatin, 500 mg/l carbenicillin, 100 mg/l kanamycin and 0.7% agar for 8 to 10 weeks. Carbenicillin was used for 2 to 3 months (until the plants were potted in soil) in all media as a counter-selection to rid the plants of viable *Agrobacterium tumefaciens cells*.

EXAMPLE 5

RNAase Protection Assays for the Detection of AdoMetase mRNA

Tomato fruits at various stages of development from transgenic plants and wild-type plants were used as mRNA sources. mRNA was extracted from tomato cells and purified using the "QUICK PREP RNA" kit from Pharmacia, Inc (Piscataway, N.J.). Alternatively, total RNA was isolated using a LiCl precipitation procedure. Tissues were frozen in liquid nitrogen and ground to a fine powder. 550 μl phenol/ buffer (1:1, Tris-saturated phenol, pH 6.9: Extraction buffer (100 mM LiCl, 100 mM Tris-HCl pH 8.0, 10 mM EDTA, 1% SDS)) at 80° C. was added for every 100 mg of the powder. The mixture was vortexed for 60 seconds, 250 μl chloroform was added, the mixture vortexed for another 30 seconds, and spun to separate the phases. The aqueous phase was removed to a new tube, an equal volume of 4M LiCl was added and mixed, and the sample was placed at −20° C. for 2 to 24 hours. The RNA was pelleted, washed and resuspended in water.

RNAse Protection Assays (RPA) were performed following the manufacturer's instructions using an "RPAII" kit from Ambion, Inc. (Hialeah, Fla.), as previously described by Lee, et al.

Plasmid pAG-924 was used to generate $^{32}$P-UTP-labeled RNA probe using bacteriophage T7 RNA polymerase as contained in the "RIBOPROBE II T7 RNA POLYMERASE SYSTEM" from Promega, Inc. The radiolabeled probe was purified on a preparative polyacrylamide gel and used for up to one week.

One microgram of isolated mRNA was hybridized to approximately 10,000 CPM of the RNA probe and further processed as per the instructions in the "RPA II" kit. Briefly, between 0.7 and 1.0 nanogram of the purified MRNA was mixed with 10,000 CPM of the $^{32}$P-RNA probe in a total volume of 15 μl. 20 μl of a hybridization buffer that allows hybridization of complementary sequences (Ausubel, et al.; Maniatis, et al.; Sambrook, et al.) is then added. The hybridization solution is provided in the "RPAII" kit from Ambion (Hialeah, Fla.). The solution was heated to 90° C. for 3–4 minutes to denature all the RNA and incubated at 45° C. overnight to allow hybridization of complementary sequences. The solution was cooled to 37° C. and RNase (provided in the Ambion kit), which degrades all unhybridized probe, was added.

Protected probe was resolved on a denaturing polyacrylamide gel, dried, and exposed to film for up to 3 hours. Quantitative analysis of the RPA signals was accomplished by excising each band from the gel, dissolving the band in a liquid fluor, and determining the radioactivity present in the sample using liquid scintillation counting. A standard curve was generated using various amounts of unlabeled RNA synthesized from a AdoMetase fragment cloned into pGEM5Z(+) in the sense orientation. The linear range of the assay was dependent on the amount of input $^{32}$P-labeled RNA probe in the RNAase protection assay but typically ranged from 10 pg to 1 ng of mRNA.

EXAMPLE 6

Ethylene Measurements

A. Leaf disks

Measurement of ethylene from leaf discs was performed by excising five one-centimeter leaf discs from mature tomato leaves and placing them in a 25 ml Erlenmeyer flask on top of filter paper saturated with Murishige and Skoog (MS) medium or MS medium supplemented with 10 μM of the auxin naphthalene acetic acid (NAA).

B. Fruit

The assay for tomato ethylene evolution was performed by sealing glass jars containing individual fruit for a 0.5 to 1.0 hour period and sampling 2 ml aliquots for gas chromatographic analysis.

B. Ethylene measurements

Ethylene evolution was measured by gas chromatography/flame ionization after 20 hours and recorded as nanoliters of ethylene/gram fresh weight/hour. A Hewlett Packard 5890 (Palo Alto, Calif.) gas chromatograph with a flame ionization detector and a 6 ft Porapak N column was used for all ethylene measurements (Adams, et al., Ward, et al.). This system combined with an HP Vectra computer and the current version of "CHEMSTATION" (Hewlett Packard) allows measurement of ethylene concentrations as low as 0.2 nl of ethylene in a 2 ml sample (0.1 ppm).

Following measurement of the ethylene in the headspace, the values were converted to nanoliters of ethylene per gram of tissue per hour.

EXAMPLE 7

Western Blot Analysis

Frozen tomato tissues were ground in liquid nitrogen, extracted directly into Lammeli sample buffer (50 mM Tris, pH 6.8, 1% SDS, 5% betamecaptoethaon, 10% glycerol, and 0.005% bromophenol blue), heated to 95° C. for 5 minutes and centrifuged to remove debris. Total soluble protein in the supernatants was measured using the Coomassie Plus protein assay (Pierce, Rockford, Ill.). Eight micrograms of soluble protein from each sample, or known quantities of purified AdoMetase (positive control) were resolved on a polyacrylamide gel and electrophoretically transferred to Immobilon-P membrane using standard procedures. The blot was incubated with 2 μg/ml of the SAM10-9A3.1.3 monoclonal antibody to SAMase (Goding) in PBS-Tween (phosphate-buffered saline, 0.05% Tween 20), 1% bovine serum albumin (BSA) buffer for 60 minutes at 25° C. The blot was then washed 4 times in PBS-Tween buffer and incubated for 60 minutes with a goat antimouse HRP-conjugate suspended in PBS-Tween, 1% BSA buffer (Kirkegaard and Perry Laboratories, Inc., Gaithersburg, Md.). Bound antibody was detected using the Renaissance chemiluminescence reagent (DuPont NEN, Boston, Mass.) according to the manufacturer's instructions.

EXAMPLE 8

Characterization of Transgenic Tomato Plants

A. Promoter Effect on AdoMetase mRNA Levels in Wounded Leaves.

Fresh and wounded leaves from six independent transgenic plants, E4-1, E4-2, E4-3, E4-4, E4-5 and E4-6, were assayed for AdoMetase mRNA levels. All transgenic lines contained the E4 promoter adjacent the AdoMetase gene.

Single, freshly detached leaves were wounded by cutting 6–7 times with a dull knife. Two hours after wounding the total RNA was extracted, reacted and analyzed as described in Example 5. Fresh leaves were dropped directly into liquid nitrogen immediately after picking to halt RNAse activity, and processed as above.

The products of the RNA protection assay were resolved on polyacrylamide gels and exposed to X-ray film. A representative autoradiogram of the RNA protection assay is presented in FIG. 7A. As can be seen in the figure, expression of SAMase is silent in normal tomato plant leaves (fresh and wounded) and in fresh leaves isolated from transgenic plants. Expression of AdoMetase RNA is clearly evident, however, in wounded leaves from four of the six transgenic lines.

The level of AdoMetase mRNA was quantitated as described in Example 5 by liquid scintillation counting. FIG. 7B presents the results of this analysis, shown as a ratio of wound inducibility, for four of the lines shown in FIG. 7A (E4-2, E4-4, E4-5 and E4-6), along with four other lines (E4-8, E4-10, E4-12 and E4-13). The results are consistent with those shown in FIG. 7A, and indicate that a transgene driven by an E4 promoter can be activated in plant tissues by the wounding of those tissues, in other words, that the E4 promoter is wound-inducible.

B. Promoter Effect on Ethylene Production in Wounded Leaves.

A leaf disc ethylene production assay was conducted, as detailed in Example 6, to measure the impact of wound-induced AdoMetase expression on wound-induced ethylene synthesis expected from these tissues. Leaves from a normal (M) and four transgenic (E4-2, E4-4, E4-5 and E4-12) tomato plants were cut with a cork bore into one cm discs that were measured for their ability to release ethylene.

Table 1 summarizes ethylene synthesis in leaves from control and four transgenic lines 4.5 and 19 hours after wounding. Leaves from two of the pAG-5520 transgenic lines were significantly reduced in their ability to produce ethylene. Lines E4-4 and E4-5 produced 69.6% and 84.8%, respectively, of the ethylene produced by the control plants during the first 4.5 hours. The ethylene reduction in those two lines were greater from 4.5 to 19 hours during which they produced 54.4% and 45.6%, respectively, of the controls. The data in this table are also presented in FIG. 8 in graphical form.

TABLE 1

WOUND-INDUCED ETHYLENE SYNTHESIS IN pAG-5520 TRANSGENIC PLANTS

| Plant ID | 4.5 hr. (nl/g/hr) | 4.5 to 19 hr. (nl/g/hr) |
|---|---|---|
| Control | 17.1 ± 2.7 | 5.7 ± 1.6 |
| E4-2 | 20.2 ± 0.42 | 5.1 ± 1.5 |
| E4-4 | 11.9 ± 1.3 | 3.1 ± 0.6 |
| E4-5 | 14.5 ± 0.5 | 2.6 ± 0.4 |
| E4-12 | 21.1 ± 5.1 | 5.4 ± 1.4 |

Error values are one standard deviation of the data (n = 3).

C. Adometase mRNA Expression in Ripening Transgenic Fruit.

Expression of AdoMetase in ripening pAG-5520 tomato fruit was measured using an RNAse protection assay (RPA), as detailed in Example 5. Ripening fruit were harvested at four different stages, mature green (MG), breaker (Br), orange (Or) and ripe (Ri).

FIG. 9 displays the AdoMetase RNA expression level at each of these stages. FIG. 10 is a graphical representation of the same data, quantitated as described in Example 5 by liquid scintillation counting. Two of the transgenic lines assayed showed little or no expression of AdoMetase. Six other lines showed significant AdoMetase RNA expression, with the orange stage being predominant. In five of the six lines expressing AdoMetase, the expression level at the ripe stage was substantially diminished, demonstrating the transient nature of the E4-directed expression.

D. Western Blot Analysis of AdoMetase Expression.

Western blot analysis was carried out on protein extracts from E4-5 transgenic ripening tomatoes as detailed in Example 7. The results are shown in FIG. 11.

FIG. 11 shows the level of AdoMetase at four stages of fruit ripening. The pattern of expression matches that of AdoMetase transcription, including a decline in AdoMetase at the ripe stage. Known quantities of purified recombinant AdoMetase were run in the control lanes and used to establish a standard curve based on signal intensity. This allowed estimation of the relative amount of AdoMetase in these tomatoes and was calculated to be approximately 0.05% of the total soluble protein at the orange stage of ripening.

E. Ethylene Production in Ripening Transgenic Fruit.

Daily ethylene production by control and pAG-5520 transgenic fruit picked at the breaker stage was measured by sealing glass jars containing individual fruit and sampling 2 ml aliquots for gas chromatographic analysis, as detailed in Example 6. Measurements were made over a period of 15 days post-harvest.

The results of the analysis are presented in FIG. 12, which shows a comparison of fruit from one pAG-5520 transgenic line (E4-05) with the fruit from untransformed controls. The control values are represented as open squares, whereas the values from the transgenic line are represented as diamonds. The values are the average of ethylene determinations for three fruit. Error bars represent one standard deviation of the data.

In the transgenic line, the rate of ethylene production declines steeply immediately after harvest, reaching a minimum of approximately 1.0 nl/g/h at 7 days postharvest. After this point, the rate increases to a level of approximately 2 to 3-fold the minimum and remains relatively constant. The kinetics of ethylene production from these transgenic tomatoes correlates with the observed AdoMetase RNA transcription and AdoMetase accumulation in the corresponding fruit. When AdoMetase expression is high the level of ethylene production is low, as expected.

The data represent a time period of fifteen days after the breaker stage of fruit ripening (post-breaker), and demonstrate a reduction in the amount of ethylene production in transgenic tomatoes versus normal fruit over the fifteen day period. Further, the data graphically illustrate the biological consequence of the transient nature of E4-driven Adometase expression described above.

The effect of AdoMetase gene expression on ripening has several dimensions, including (i) pAG-5520 tomatoes (transgenic line E4-12-D) develop color to a light red stage and then cease further color development, and (ii) the transgenic tomatoes remain firm for much longer than controls.

While the invention has been described with reference to specific methods and embodiments, it will be appreciated that various modifications and changes may be made without departing from the invention.

It is claimed:

1. A method for delaying wound-induced ripening of fruit of a fruit-bearing plant, comprising transforming progenitor cells of the plant with a selectable vector containing (i) a promoter of a tomato E4 gene, wherein said tomato E4 gene is composed of a series of nucleotides which is at least 60% identical to that presented in SEQ ID NO:8, and where said promoter is capable of inducing transient, wound-induced expression of a gene under its control, and (ii) a heterologous S-adenosylmethionine hydrolase gene under the control of the promoter, growing the transformed progenitor cells to produce a transgenic plant bearing fruit, and subjecting the fruit to a wound, whereby the ripening of said fruit is delayed.

2. The method of claim 1, wherein said subjecting comprises picking the fruit from the transgenic plant.

3. The method of claim 1, wherein the transgenic plant is selected from the group consisting of tomato, raspberry, strawberry and melon.

4. The method of claim 1, wherein the promoter has the nucleotide sequence of nucleotides 1 to 1173 of SEQ ID NO:10.

5. A delayed-ripening fruit, containing (i) a heterologous S-adenosylmethionine hydrolase gene, and (ii) a promoter of a tomato E4 gene operably linked to said heterologous gene, wherein said tomato E4 gene is composed of a series of nucleotides which is at least 60% identical to that presented in SEQ ID NO:8, and where said promoter is effective to produce transient expression of the gene when the fruit is picked.

6. The fruit of claim 5, wherein the fruit is selected from the group consisting of tomato, raspberry, strawberry and melon.

7. A method for inducing transient, wound-induced expression of a heterologous S-adenosylmethionine hydrolase gene in fruit of a fruit-bearing plant, comprising transforming progenitor cells of the plant with a selectable vector containing (i) a promoter of a tomato E4 gene, wherein said tomato E4 gene is composed of a series of nucleotides which is at least 60% identical to that presented in SEQ ID NO:8, and where said promoter is capable of inducing transient, wound-induced expression of a gene under its control, and (ii) a heterologous S-adenosylmethionine hydrolase gene under the control of the promoter, growing the transformed progenitor cells to produce a transgenic plant bearing fruit, and subjecting the fruit to a wound, whereby the expression of said S-adenosylmethionine hydrolase gene is transiently induced in said fruit.

8. The method of claim 7, wherein said subjecting comprises picking the fruit from the transgenic plant.

9. The method of claim 7, wherein the fruit-bearing plant is selected from the group consisting of tomato, raspberry, strawberry and melon.

10. The method of claim 7, wherein the promoter has a nucleotide sequence of nucleotides 1 to 1173 of SEQ ID NO:10.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
      ( A ) LENGTH: 39 base pairs
      ( B ) TYPE: nucleic acid
      ( C ) STRANDEDNESS: single
      ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
      ( C ) INDIVIDUAL ISOLATE: Fig. 3 - top strand of synthetic
         oligo ( i x ) FEATURE:
      ( A ) NAME/KEY: CDS
      ( B ) LOCATION: 12..38

( x i ) SEQUENCE DESCRIPTION: SEQ ID NO:1:

```
GATCCGCCAC C ATG GTT TTC ACT AAA GAG CCT GCG AAC G         39
            Met Val Phe Thr Lys Glu Pro Ala Asn
             1               5
```

( 2 ) INFORMATION FOR SEQ ID NO:2:

( i ) SEQUENCE CHARACTERISTICS:
      ( A ) LENGTH: 9 amino acids
      ( B ) TYPE: amino acid
      ( D ) TOPOLOGY: linear ( i i ) MOLECULE TYPE: protein ( x i ) SEQUENCE DESCRIPTION: SEQ ID NO:2:

```
Met Val Phe Thr Lys Glu Pro Ala Asn
 1               5
```

( 2 ) INFORMATION FOR SEQ ID NO:3:

( i ) SEQUENCE CHARACTERISTICS:
      ( A ) LENGTH: 35 base pairs
      ( B ) TYPE: nucleic acid
      ( C ) STRANDEDNESS: single
      ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
      ( C ) INDIVIDUAL ISOLATE: Fig.3, bottom strand of synthetic
         oligo ( x i ) SEQUENCE DESCRIPTION: SEQ ID NO:3:

```
CGTTCGCAGG CTCTTTAGTG AAAACCATGG TGGCG          35
```

( 2 ) INFORMATION FOR SEQ ID NO:4:

( i ) SEQUENCE CHARACTERISTICS:
      ( A ) LENGTH: 26 base pairs
      ( B ) TYPE: nucleic acid (C) STRANDEDNESS: single
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Fig. 4 - E4 promoter, 5'primer (xi) SEQUENCE DESCRIPTION: SEQ ID NO:4:

AGCCCATTGA AGCTTAAAGT AAACTT    26

(2) INFORMATION FOR SEQ ID NO:5:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Fig. 4 - E4 promoter, 3'primer (xi) SEQUENCE DESCRIPTION: SEQ ID NO:5:

TACCCTCCAT GGCTCAATCT CT    22

(2) INFORMATION FOR SEQ ID NO:6:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: E4 gene 5'primer (xi) SEQUENCE DESCRIPTION: SEQ ID NO:6:

ACGCATGGAG GGTAACAA    18

(2) INFORMATION FOR SEQ ID NO:7:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: tomato E4 gene 3'primer (xi) SEQUENCE DESCRIPTION: SEQ ID NO:7:

GAAGCAAGAC AGCAAATG                                                                                          18

( 2 ) INFORMATION FOR SEQ ID NO:8:

( i ) SEQUENCE CHARACTERISTICS:
        ( A ) LENGTH: 2796 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: Fig. 13 - E4 tomato gene DNA ( i x ) FEATURE:
        ( A ) NAME/KEY: CDS
        ( B ) LOCATION: 1439..1774

( i x ) FEATURE:
        ( A ) NAME/KEY: exon
        ( B ) LOCATION: 1439..1774

( i x ) FEATURE:
        ( A ) NAME/KEY: CDS
        ( B ) LOCATION: 1859..2113

( i x ) FEATURE:
        ( A ) NAME/KEY: exon
        ( B ) LOCATION: 1859..2113

( i x ) FEATURE:
        ( A ) NAME/KEY: intron
        ( B ) LOCATION: 1775..1858

( x i ) SEQUENCE DESCRIPTION: SEQ ID NO:8:

```
GAATTCTCAA TTGAGCCCAA TTCAATCTCC AATTTCAACC CGTTTTAAAA CTTTTTATTA        60
AGATATGTTT CTATATTGAA AGTATGAATT ATTATCTATT TAACATCTTT TAGGATTTAT       120
CTATCCATTT GCTACTTTTT TAACAAAAAA TTCTTGAGTG AAAATTCAAA TTGTGATTAT       180
AAAAGTTAAA TATCAATATG TTAAATTATT AAGATTAATC GGGTCAAATT GGCGGGTCAA       240
GGCCCAATTC TTTTTTAGCC CATTTAAGCT CAAAGTAAAC TTGGGTGGGT CAAGACCCAA       300
CTCGATTTCT GTTCAACCCA TTTTAATATT TCTATTTTCA ACCTAACCCG CTCATTTGAT       360
ACCCCTACAA ATATCATATT TGTGTGTGAA ATATTTTTTG GGCTGGAGAG AGAGGCCCCG       420
AGGGGAGTGG AGGGGTGGGG TGGGGAGAGA GAGCGAGAAA GAGTGGAGAG AGAAATTTGA       480
TATGAAATCC TACATATATT ACAGATTGTA ATGTTCTAAA CTATAACGAT TTGTCATAAA       540
CACATATCAT GGATTTGTCT TTTTGTGTAA TTTTCCCAAT TGTAAATAGG ACTTCGTTAT       600
TTGAAACTTG AAAGTGAAGT CACATAGATT AAGTACAAAC ATTAATTAAA GACCGTGGTG       660
GAATGATAAA TATTTATTTA TCTTTAATTA GTTATTTTTT TGGGAGCTCT TTATTCCAAT       720
GTGAGACTTT TGCGACATAT ATTCAAATTT AATCGAATCA CAATATGTAT TAGATTGATA       780
AAAAAATAAT TTTTTTACAA TGTTAGTTGA GACTCATAAC TTACTGCCTA TTGGTAATCT       840
ATGACTCCTA ATTCCTTAAT TATTTAAATA TATCATCTTG ATCGTTAACA AAGTAATTTC       900
GAAAGACCAC GAGTAAGAAG ACAAACGAGA ATACCAAAAA ATTCAAAAAT TTAATGTGAT       960
TTGGTCAATC GATCTACGTC CATAAAGGAG ATGAGTAATC TACTATAAAT ATGAGAGTAC      1020
AAAATACAGA GAGAAACAAC CTCAACTAAT TCACTCGGAA TACATGAGAA GTTCACACAA      1080
GTGATAACGT ATCAAACTTG TGACCCACAC TTTTCCCTCT AACCAAAGCT CTTAAAACTA      1140
```

```
TATTGTGAAT GCTGATTAAG TTAAACGAAA CAGTCCTAAA TCTTTTCCGT CCTATGAGAA          1200
ACAAGATTAA TCAATTCACA ATTTTTTTAA AAAGAAAAAC CTGTAAGAAA TTTAGGCAAA          1260
CAAAACCTAA CACAAGTTTG TTTTTGTTTT TACTACCAAC AAGAAATTCA AATGGCAAAT          1320
GTATAACGCA TCTTAGCTAA TTATATGACC AGATTCAGAT TAATATACAT CTTCACCCAT          1380
GCAATCCATT TCTATATAAA GAAACATACA CGAACTTGAT ATTATTAGAG ATTGAGCA            1438
ATG GAG GGT AAC AAC AGC AGT AGC AAG TCA ACC ACC AAT CCA GCA TTG            1486
Met Glu Gly Asn Asn Ser Ser Ser Lys Ser Thr Thr Asn Pro Ala Leu
 1               5                   10                  15
GAT CCG GAT CTG GAC AGC CCG GAT CAG CCG GGT CTG GAG TTT GCC CAA            1534
Asp Pro Asp Leu Asp Ser Pro Asp Gln Pro Gly Leu Glu Phe Ala Gln
            20                  25                  30
TTT GCT GCC GGC TGC TTT TGG GGA GTC GAA TTG GCT TTC CAG AGG GTT            1582
Phe Ala Ala Gly Cys Phe Trp Gly Val Glu Leu Ala Phe Gln Arg Val
        35                  40                  45
GGA GGA GTA GTG AAG ACG GAG GTT GGG TAC TCT CAG GGG AAT GTC CAT            1630
Gly Gly Val Val Lys Thr Glu Val Gly Tyr Ser Gln Gly Asn Val His
    50                  55                  60
GAC CCG AAC TAC AAG CTT ATT TGC TCC GGA ACA ACC GAA CAT GCC GAG            1678
Asp Pro Asn Tyr Lys Leu Ile Cys Ser Gly Thr Thr Glu His Ala Glu
 65                 70                  75                  80
GCC ATT CGG ATC CAG TTT GAC CCG AAT GTC TGC CCG TAT TCC AAT CTC            1726
Ala Ile Arg Ile Gln Phe Asp Pro Asn Val Cys Pro Tyr Ser Asn Leu
            85                  90                  95
CTT TCT CTA TTT TGG AGT CGC CAT GAC CCG ACC ACT CTA AAT CGC CAG            1774
Leu Ser Leu Phe Trp Ser Arg His Asp Pro Thr Thr Leu Asn Arg Gln
        100                 105                 110
GTATCAAATT CCTTTGGTGT TTCATTTTAT GTGATTAATA TTAAAAATTT TTTATATAAA          1834
TGTCATGATG ATGGTTGTTG CTAG GGT AAT GAT GTG GGA AAG CAA TAC CGC            1885
                           Gly Asn Asp Val Gly Lys Gln Tyr Arg
                            1               5
TCA GGA ATA TAT TAC TAT AAT GAT GCT CAG GCT CAA CTG GCA AGG GAG            1933
Ser Gly Ile Tyr Tyr Tyr Asn Asp Ala Gln Ala Gln Leu Ala Arg Glu
 10              15                  20                  25
TCG TTA GAA GCT AAG CAG AAG GAA TTT ATG GAT AAG AAA ATT GTC ACT            1981
Ser Leu Glu Ala Lys Gln Lys Glu Phe Met Asp Lys Lys Ile Val Thr
            30                  35                  40
GAA ATT CTT CCT GCT AAG AGA TTT TAT AGA GCT GAA GAG TAT CAC CAG            2029
Glu Ile Leu Pro Ala Lys Arg Phe Tyr Arg Ala Glu Glu Tyr His Gln
        45                  50                  55
CAA TAT CTA GAG AAG GGT GGG GGC AGA GGT TGT AAG CAG TCG GCT GCA            2077
Gln Tyr Leu Glu Lys Gly Gly Gly Arg Gly Cys Lys Gln Ser Ala Ala
    60                  65                  70
AAG GGC TGC AAT GAC CCA ATA AGG TGC TAC GGT TGACAGCAGA TCTTTGAATG          2130
Lys Gly Cys Asn Asp Pro Ile Arg Cys Tyr Gly
 75                 80                      85
TCATAGCAAC TACAAAAGAA CTTGTTAGAC ATTTGCTGTC TTGCTTCTTT AAATTTGAAT          2190
AAACATGACA ATGATTCTTA TAACTACTTG CTCTCTTGGA TGGAATAACT AGTTGTCGTA          2250
AAGTATTCTC CTCTTGCTAA TTATTATCTC TCTTTATATG GTACCTGCAA TTTGTTGCTT          2310
TAGTTACAGA ATAATGGACG TCAATTCTAT ATCTTAATTT GTTTAAGTC TTAAATGAGG           2370
TGGTTTGTGT TTGAAAGCAA TATCAAGCAT AGTAATACCA ATGATTTAGT AGATGAACTT          2430
AATCAAATCA AATTCCAAAA TGCAGTCTAC AAATTGACAA CATGAAGTTA AGTGTATCTT          2490
ATGTAAATTG ACATCTTTCC TAGTAGATGC CTAATACTTT TGTAAAGACT AAAATAAGCA          2550
CAGATGAGGC TTGTGCATTT AACTTAGAGT TCATCCTTAG GTGTGGCTGC AGGAGACCCT          2610
```

```
GTAGGGTTGC TTGAAGTCTT GATGGGGTAG GAGGGTTGCA TTGCTATACC ACACAACCCC      2670

TCTTCAGCGT CAACCTTGCG CTGCATTCTA ATGTATCCTT TTTCTCCCCA TTCAGCTCCC      2730

CATGAGTTCT TCACAATCCA GTATTTGGTT CCATCGACGG TTGTGCCATA CCCCACAATA      2790

GCCACA                                                                 2796
```

( 2 ) INFORMATION FOR SEQ ID NO:9:

( i ) SEQUENCE CHARACTERISTICS:
        ( A ) LENGTH: 196 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Met Glu Gly Asn Asn Ser Ser Ser Lys Ser Thr Thr Asn Pro Ala Leu
 1               5                  10                  15

Asp Pro Asp Leu Asp Ser Pro Asp Gln Pro Gly Leu Glu Phe Ala Gln
            20                  25                  30

Phe Ala Ala Gly Cys Phe Trp Gly Val Glu Leu Ala Phe Gln Arg Val
        35                  40                  45

Gly Gly Val Val Lys Thr Glu Val Gly Tyr Ser Gln Gly Asn Val His
    50                  55                  60

Asp Pro Asn Tyr Lys Leu Ile Cys Ser Gly Thr Thr Glu His Ala Glu
65                  70                  75                  80

Ala Ile Arg Ile Gln Phe Asp Pro Asn Val Cys Pro Tyr Ser Asn Leu
                85                  90                  95

Leu Ser Leu Phe Trp Ser Arg His Asp Pro Thr Thr Leu Asn Arg Gln
            100                 105                 110

Gly Asn Asp Val Gly Lys Gln Tyr Arg Ser Gly Ile Tyr Tyr Tyr Asn
        115                 120                 125

Asp Ala Gln Ala Gln Leu Ala Arg Glu Ser Leu Glu Ala Lys Gln Lys
    130                 135                 140

Glu Phe Met Asp Lys Lys Ile Val Thr Glu Ile Leu Pro Ala Lys Arg
145                 150                 155                 160

Phe Tyr Arg Ala Glu Glu Tyr His Gln Gln Tyr Leu Glu Lys Gly Gly
                165                 170                 175

Gly Arg Gly Cys Lys Gln Ser Ala Ala Lys Gly Cys Asn Asp Pro Ile
            180                 185                 190

Arg Cys Tyr Gly
            195
```

( 2 ) INFORMATION FOR SEQ ID NO:10:

( i ) SEQUENCE CHARACTERISTICS:
        ( A ) LENGTH: 1678 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Fig. 14 - E4 tomato promoter /
           AdoMetase gene DNA ( i x ) FEATURE:
        ( A ) NAME/KEY: CDS ( B ) LOCATION: 1174..1629

( x i ) SEQUENCE DESCRIPTION: SEQ ID NO:10:

| | | | | | | |
|---|---|---|---|---|---|---|
| AAGCTTAAAG | TAAACTTGGG | TGGGTCAAGA | CCCAACTCGA | TTTCTGTTCA | ACCCATTTTA | 60 |
| ATATTTCTAT | TTTCAACCTA | ACCCGCTCAT | TTGATACCCC | TACAAATATC | ATATTTGTGT | 120 |
| GTGAAATATT | TTTTGGGCTG | GAGAGAGAGG | CCCCGAGGGG | AGTGGAGGGG | TGGGGTGGGG | 180 |
| AGAGAGAGCG | AGAAAGAGTG | GAGAGAGAAA | TTTGATATGA | AATCCTACAT | ATATTACAGA | 240 |
| TTGTAATGTT | CTAAACTATA | ACGATTTGTC | ATAAACACAT | ATCATGGATT | TGTCTTTTTG | 300 |
| TGTAATTTTC | CCAATTGTAA | ATAGGACTTC | GTTATTGAA | ACTTGAAAGT | GAAGTCACAT | 360 |
| AGATTAAGTA | CAAACATTAA | TTAAAGACCG | TGGTGGAATG | ATAAATATTT | ATTTATCTTT | 420 |
| AATTAGTTAT | TTTTTTGGGA | GCTCTTTATT | CCAATGTGAG | ACTTTTGCGA | CATATATTCA | 480 |
| AATTTAATCG | AATCACAATA | TGTATTAGAT | TGATAAAAAA | ATAATTTTTT | TACAATGTTA | 540 |
| GTTGAGACTC | ATAACTTACT | GCCTATTGGT | AATCTATGAC | TCCTAATTCC | TTAATTATTT | 600 |
| AAATATATCA | TCTTGATCGT | TAACAAAGTA | ATTCGAAAG | ACCACGAGTA | AGAAGACAAA | 660 |
| CGAGAATACC | AAAAAATTCA | AAAATTTAAT | GTGATTTGGT | CAATCGATCT | ACGTCCATAA | 720 |
| AGGAGATGAG | TAATCTACTA | TAAATATGAG | AGTACAAAAT | ACAGAGAGAA | ACAACCTCAA | 780 |
| CTAATTCACT | CGGAATACAT | GAGAAGTTCA | CACAAGTGAT | AACGTATCAA | ACTTGTGACC | 840 |
| CACACTTTTC | CCTCTAACCA | AAGCTCTTAA | AACTATATTG | TGAATGCTGA | TTAAGTTAAA | 900 |
| CGAAACAGTC | CTAAATCTTT | TCCGTCCTAT | GAGAAACAAG | ATTAATCAAT | TCACAATTTT | 960 |
| TTTAAAAAGA | AAAACCTGTA | AGAAATTTAG | GCAAACAAAA | CCTAACACAA | GTTTGTTTTT | 1020 |
| GTTTTTACTA | CCAACAAGAA | ATTCAAATGG | CAAATGTATA | ACGCATCTTA | GCTAATTATA | 1080 |
| TGACCAGATT | CAGATTAATA | TACATCTTCA | CCCATGCAAT | CCATTTCTAT | ATAAAGAAAC | 1140 |

| | | | | | | | | |
|---|---|---|---|---|---|---|---|---|
| ATACACGAAC | TTGATATTAT | TAGAGATTGA | GCC | ATG | GTT | TTC | ACT | AAA GAG CCT | 1194 |
| | | | | Met | Val | Phe | Thr | Lys Glu Pro | |
| | | | | 1 | | | | 5 | |

| | | | | | | | | | | | | | | | |
|---|---|---|---|---|---|---|---|---|---|---|---|---|---|---|---|
| GCG | AAC | GTC | TTC | TAT | GTA | CTG | GTT | TCC | GCT | TTC | CGT | TCT | AAC | CTC | TGC | 1242 |
| Ala | Asn | Val | Phe | Tyr | Val | Leu | Val | Ser | Ala | Phe | Arg | Ser | Asn | Leu | Cys | |
| | | 10 | | | | 15 | | | | | 20 | | | | | |

| GAT | GAG | GTG | AAT | ATG | AGC | AGA | CAC | CGC | CAC | ATG | GTA | AGC | ACT | TTA | CGT | 1290 |
|---|---|---|---|---|---|---|---|---|---|---|---|---|---|---|---|---|
| Asp | Glu | Val | Asn | Met | Ser | Arg | His | Arg | His | Met | Val | Ser | Thr | Leu | Arg | |
| | 25 | | | | 30 | | | | | 35 | | | | | | |

| GCC | GCA | CCG | GGT | CTT | TAT | GGC | TCC | GTT | GAG | TCA | ACC | GAT | TTG | ACC | GGG | 1338 |
|---|---|---|---|---|---|---|---|---|---|---|---|---|---|---|---|---|
| Ala | Ala | Pro | Gly | Leu | Tyr | Gly | Ser | Val | Glu | Ser | Thr | Asp | Leu | Thr | Gly | |
| 40 | | | | | 45 | | | | 50 | | | | | | 55 | |

| TGC | TAT | CGT | GAG | GCA | ATC | TCA | AGC | GCA | CCA | ACT | GAG | GAA | AAA | ACT | GTT | 1386 |
|---|---|---|---|---|---|---|---|---|---|---|---|---|---|---|---|---|
| Cys | Tyr | Arg | Glu | Ala | Ile | Ser | Ser | Ala | Pro | Thr | Glu | Glu | Lys | Thr | Val | |
| | | | 60 | | | | | 65 | | | | | 70 | | | |

| CGT | GTA | CGC | TAC | AAG | GAC | AAA | GCG | CAG | CCA | CTC | AAT | GTT | GCA | CGC | CTA | 1434 |
|---|---|---|---|---|---|---|---|---|---|---|---|---|---|---|---|---|
| Arg | Val | Arg | Tyr | Lys | Asp | Lys | Ala | Gln | Pro | Leu | Asn | Val | Ala | Arg | Leu | |
| | | 75 | | | | | 80 | | | | | 85 | | | | |

| GCT | TCT | AAT | GAG | TGG | GAG | CAA | GAT | TGC | GTA | CTG | GTA | TAC | AAA | TCA | CAG | 1482 |
|---|---|---|---|---|---|---|---|---|---|---|---|---|---|---|---|---|
| Ala | Ser | Asn | Glu | Trp | Glu | Gln | Asp | Cys | Val | Leu | Val | Tyr | Lys | Ser | Gln | |
| | | 90 | | | | | 95 | | | | | 100 | | | | |

| ACT | CAC | ACG | GCT | GGT | CTG | GTG | TAC | GCT | AAA | GGT | ATC | GAC | GGG | TAT | AAG | 1530 |
|---|---|---|---|---|---|---|---|---|---|---|---|---|---|---|---|---|
| Thr | His | Thr | Ala | Gly | Leu | Val | Tyr | Ala | Lys | Gly | Ile | Asp | Gly | Tyr | Lys | |
| 105 | | | | | 110 | | | | | 115 | | | | | | |

| GCT | GAA | CGT | CTG | CCG | GGT | AGT | TTC | CAA | GAG | GTT | CCT | AAA | GGC | GCA | CCG | 1578 |
|---|---|---|---|---|---|---|---|---|---|---|---|---|---|---|---|---|
| Ala | Glu | Arg | Leu | Pro | Gly | Ser | Phe | Gln | Glu | Val | Pro | Lys | Gly | Ala | Pro | |
| 120 | | | | 125 | | | | | 130 | | | | | | 135 | |

| CTG | CAA | GGC | TGC | TTC | ACT | ATT | GAT | GAG | TTC | GGT | CGC | CGC | TGG | CAA | GTA | 1626 |
|---|---|---|---|---|---|---|---|---|---|---|---|---|---|---|---|---|
| Leu | Gln | Gly | Cys | Phe | Thr | Ile | Asp | Glu | Phe | Gly | Arg | Arg | Trp | Gln | Val | |

|  | 140 |  | 145 |  | 150 |  |
|---|---|---|---|---|---|---|
| CAA | TAACGTGTTA | AACTCAAGGT | CATGCACGAT | GCGTGGCGGA | TCGGGTACC | 1678 |
| Gln |

( 2 ) INFORMATION FOR SEQ ID NO:11:

( i ) SEQUENCE CHARACTERISTICS:
        ( A ) LENGTH: 152 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

| Met | Val | Phe | Thr | Lys | Glu | Pro | Ala | Asn | Val | Phe | Tyr | Val | Leu | Val | Ser |
|---|---|---|---|---|---|---|---|---|---|---|---|---|---|---|---|
| 1 |  |  |  | 5 |  |  |  |  | 10 |  |  |  |  | 15 |  |

| Ala | Phe | Arg | Ser | Asn | Leu | Cys | Asp | Glu | Val | Asn | Met | Ser | Arg | His | Arg |
|---|---|---|---|---|---|---|---|---|---|---|---|---|---|---|---|
|  |  |  | 20 |  |  |  |  | 25 |  |  |  |  | 30 |  |  |

| His | Met | Val | Ser | Thr | Leu | Arg | Ala | Ala | Pro | Gly | Leu | Tyr | Gly | Ser | Val |
|---|---|---|---|---|---|---|---|---|---|---|---|---|---|---|---|
|  |  | 35 |  |  |  |  |  | 40 |  |  |  |  | 45 |  |  |

| Glu | Ser | Thr | Asp | Leu | Thr | Gly | Cys | Tyr | Arg | Glu | Ala | Ile | Ser | Ser | Ala |
|---|---|---|---|---|---|---|---|---|---|---|---|---|---|---|---|
|  | 50 |  |  |  |  | 55 |  |  |  |  | 60 |  |  |  |  |

| Pro | Thr | Glu | Glu | Lys | Thr | Val | Arg | Val | Arg | Tyr | Lys | Asp | Lys | Ala | Gln |
|---|---|---|---|---|---|---|---|---|---|---|---|---|---|---|---|
| 65 |  |  |  |  | 70 |  |  |  |  | 75 |  |  |  |  | 80 |

| Pro | Leu | Asn | Val | Ala | Arg | Leu | Ala | Ser | Asn | Glu | Trp | Glu | Gln | Asp | Cys |
|---|---|---|---|---|---|---|---|---|---|---|---|---|---|---|---|
|  |  |  |  | 85 |  |  |  |  | 90 |  |  |  |  | 95 |  |

| Val | Leu | Val | Tyr | Lys | Ser | Gln | Thr | His | Thr | Ala | Gly | Leu | Val | Tyr | Ala |
|---|---|---|---|---|---|---|---|---|---|---|---|---|---|---|---|
|  |  |  | 100 |  |  |  |  | 105 |  |  |  |  | 110 |  |  |

| Lys | Gly | Ile | Asp | Gly | Tyr | Lys | Ala | Glu | Arg | Leu | Pro | Gly | Ser | Phe | Gln |
|---|---|---|---|---|---|---|---|---|---|---|---|---|---|---|---|
|  |  | 115 |  |  |  |  | 120 |  |  |  |  | 125 |  |  |  |

| Glu | Val | Pro | Lys | Gly | Ala | Pro | Leu | Gln | Gly | Cys | Phe | Thr | Ile | Asp | Glu |
|---|---|---|---|---|---|---|---|---|---|---|---|---|---|---|---|
|  | 130 |  |  |  |  | 135 |  |  |  |  | 140 |  |  |  |  |

| Phe | Gly | Arg | Arg | Trp | Gln | Val | Gln |
|---|---|---|---|---|---|---|---|
| 145 |  |  |  |  | 150 |  |  |

( 2 ) INFORMATION FOR SEQ ID NO:12:

( i ) SEQUENCE CHARACTERISTICS:
        ( A ) LENGTH: 225 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: Fig. 14 - raspberry E4 gene DNA ( i x ) FEATURE:
        ( A ) NAME/KEY: CDS
        ( B ) LOCATION: 1..213

( x i ) SEQUENCE DESCRIPTION: SEQ ID NO:12:

| GAG | CTC | AGG | TTT | CAG | CGA | GTG | GCC | GGT | GTG | GTC | AAG | ACC | GAG | GTT | GGG | 48 |
|---|---|---|---|---|---|---|---|---|---|---|---|---|---|---|---|---|
| Glu | Leu | Arg | Phe | Gln | Arg | Val | Ala | Gly | Val | Val | Lys | Thr | Glu | Val | Gly |  |
| 1 |  |  |  | 5 |  |  |  |  | 10 |  |  |  |  | 15 |  |  |

| TAC | TCC | CAG | GGC | CAC | GTC | CAC | GAT | CCG | AAT | TAC | AAA | CTG | GTC | TGC | TCC | 96 |
|---|---|---|---|---|---|---|---|---|---|---|---|---|---|---|---|---|
| Tyr | Ser | Gln | Gly | His | Val | His | Asp | Pro | Asn | Tyr | Lys | Leu | Val | Cys | Ser |  |
|  |  |  | 20 |  |  |  |  | 25 |  |  |  |  | 30 |  |  |  |

| GGA | ACT | ACC | AAC | CAT | TCG | GAG | GTC | GTT | CGG | GTC | CAG | TTC | GAC | CCG | CAA | 144 |

```
Gly Thr Thr Asn His Ser Glu Val Val Arg Val Gln Phe Asp Pro Gln
         35                  40                  45

GTC TAC CCA TAC TCG GAC CTG CTT TCC GTC TTT TGG TCT CGT CAT GAT    192
Val Tyr Pro Tyr Ser Asp Leu Leu Ser Val Phe Trp Ser Arg His Asp
     50                  55                  60

CCA ACG ACT GTC AAT CGC CAG GTATGGGGAT TG                          225
Pro Thr Thr Val Asn Arg Gln
 65              70
```

( 2 ) INFORMATION FOR SEQ ID NO:13:

( i ) SEQUENCE CHARACTERISTICS:
        ( A ) LENGTH: 71 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
Glu Leu Arg Phe Gln Arg Val Ala Gly Val Val Lys Thr Glu Val Gly
 1               5                  10                  15

Tyr Ser Gln Gly His Val His Asp Pro Asn Tyr Lys Leu Val Cys Ser
             20                  25                  30

Gly Thr Thr Asn His Ser Glu Val Val Arg Val Gln Phe Asp Pro Gln
         35                  40                  45

Val Tyr Pro Tyr Ser Asp Leu Leu Ser Val Phe Trp Ser Arg His Asp
     50                  55                  60

Pro Thr Thr Val Asn Arg Gln
 65              70
```

( 2 ) INFORMATION FOR SEQ ID NO:14:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: original T3 sequence ( x i ) SEQUENCE DESCRIPTION: SEQ ID NO:14:

CACCAAATGA            10

( 2 ) INFORMATION FOR SEQ ID NO:15:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Kozak sequence ( x i ) SEQUENCE DESCRIPTION: SEQ ID NO:15:

GCCACCATGG            10